United States Patent
Oraevsky et al.

(10) Patent No.: US 9,655,594 B2
(45) Date of Patent: May 23, 2017

(54) METHODS AND COMPOSITIONS FOR TISSUE-EQUIVALENT OPTO-ACOUSTIC PHANTOMS

(71) Applicant: Seno Medical Instruments, Inc., San Antonio, TX (US)

(72) Inventors: Alexander A. Oraevsky, Houston, TX (US); Dmitri A. Tsyboulski, Houston, TX (US); Thomas G. Miller, Houston, TX (US)

(73) Assignee: SENO MEDICAL INSTRUMENTS, INC., San Antonio, TX (US)

( * ) Notice: Subject to any disclaimer, the term of this patent is extended or adjusted under 35 U.S.C. 154(b) by 359 days.

(21) Appl. No.: 14/109,816

(22) Filed: Dec. 17, 2013

(65) Prior Publication Data
US 2015/0164463 A1 Jun. 18, 2015

(51) Int. Cl.
*A61B 8/00* (2006.01)
*A61B 5/00* (2006.01)

(52) U.S. Cl.
CPC ............ *A61B 8/587* (2013.01); *A61B 5/0095* (2013.01)

(58) Field of Classification Search
None
See application file for complete search history.

(56) References Cited

U.S. PATENT DOCUMENTS

| | | |
|---|---|---|
| 4,958,626 A | 9/1990 | Nambu et al. |
| 8,839,672 B2 * | 9/2014 | Emelianov et al. ............ 73/606 |
| 2004/0099815 A1 * | 5/2004 | Sfez et al. ................ 250/492.1 |
| 2008/0076099 A1 | 3/2008 | Sarvazyan et al. |
| 2008/0261009 A1 | 10/2008 | Kawabata |
| 2009/0105588 A1 | 4/2009 | Emelianov et al. |
| 2012/0193582 A1 * | 8/2012 | Boutet et al. ............. 252/408.1 |
| 2014/0005544 A1 * | 1/2014 | Zalev et al. ................. 600/440 |

* cited by examiner

*Primary Examiner* — Robert R Raevis
(74) *Attorney, Agent, or Firm* — Harness, Dickey & Pierce, P.L.C.

(57) ABSTRACT

Methods and compositions for gelatin based tissue mimicking opto-acoustic phantom that accurately replicates opto-acoustic properties of biological tissue and permits matching of each optical and each acoustic property of specific tissues independently so that by changing one property the other property is not altered. Such phantoms can match tissue properties in the specific range of system parameters required for evaluation of hardware and software performance, calibration, validation or personnel training of optical, optoacoustic, ultrasonic or combined system used for imaging, sensing or monitoring of tissue morphology and molecular composition.

40 Claims, 31 Drawing Sheets

METHODS AND COMPOSITIONS FOR TISSUE-EQUIVALENT OPTO-ACOUSTIC PHANTOMS

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The field of present disclosure relates to phantoms replicating tissue properties, and more specifically, opto-acoustic phantoms that can be used in conjunction with optoacoustic, photo-acoustic, thermo-acoustic, optical and ultrasonic imaging, sensing and monitoring systems.

BRIEF DESCRIPTION OF THE DRAWINGS

The foregoing and other objects, features, and advantages of the invention will be apparent from the following more particular description of various embodiment of the present disclosure as illustrated in the accompanying drawings, in which reference characters refer to the same parts throughout the various views. The drawings are not necessarily to scale, emphasis instead being placed upon illustrating principles of the invention.

DETAILED DESCRIPTION

Figure 1A:
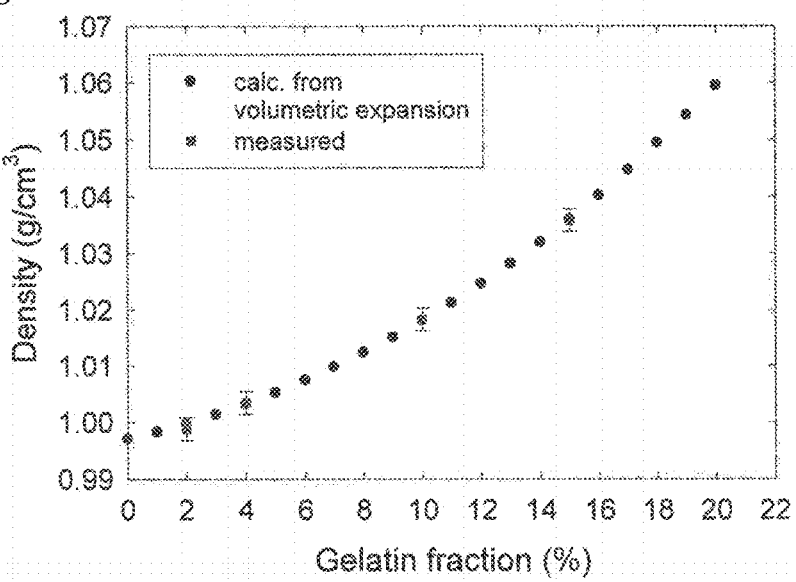
FIG. 1A illustrates an embodiment of the density of gels as a function of gelatin concentration at 25° C.
Figure 1B:
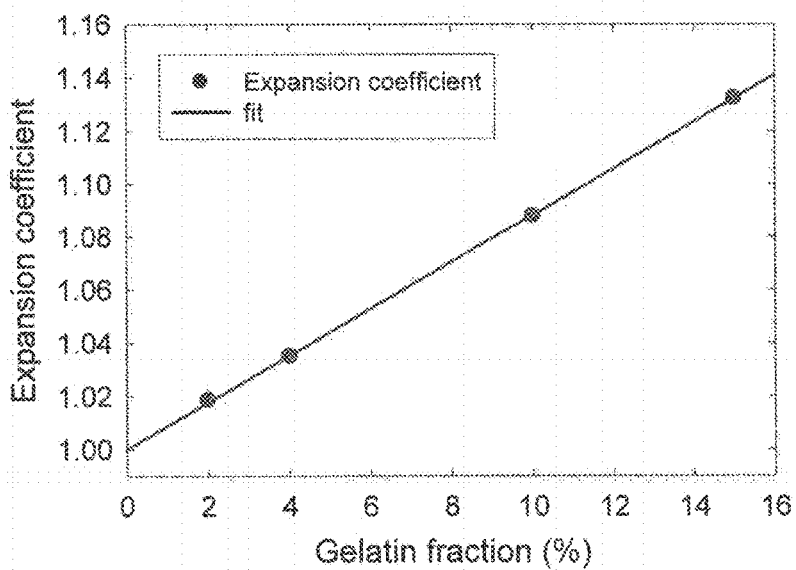
FIG. 1B illustrates an embodiment of the coefficient of volumetric expansion in gelatin hydrogels relative to water volume used to dissolve a given quantity of gelatin.

Reference will now be made in detail to various embodiments of the present invention, examples of which are illustrated in the accompanying drawings.

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Optoacoustic Imaging and Opto-Acoustic Phantoms

Optoacoustic imaging is an imaging technology based on the optoacoustic effect. When a short laser pulse is used to irradiate tissue there is local absorption of the tissue, causing heating and expansion of the tissue. The expansion of the tissue produces ultrasound that can be recorded, for example, using wide-band ultrasonic transducers (pressure sensors). The slow speed of sound in tissue (e.g., ~1,500 m/s) in comparison to the speed of light allows for the time resolved detection of these pressure waves and determination of a location from where the pressure waves originated. By analyzing information received by an array of sensors during a period following the short laser pulse, an optoacoustic image can be formed.

In various embodiments, developers of imaging and sensing systems, researchers and clinical practitioners who use optoacoustic imaging systems for purposes of diagnosis and treatment monitoring use tissue mimicking phantoms for the calibration, validation and testing pf such systems. Such phantoms can be used to simulate the optical and the acoustic properties of tissues, organs, and abnormal tissues such as tumors. Such optical and acoustic properties can include optical absorption coefficients, optical scattering coefficients, optical scattering anisotropy, speed of sound, density, acoustic impedance, acoustic attenuation and acoustic backscattering.

The phantoms and other aspects of the invention described herein are useful in connection with imaging systems such as, for example, those described in U.S. patent application Ser. No. 13/842,399 filed Mar. 15, 2013 entitled "Light Output Calibration In An Optoacoustic System," and U.S. patent application Ser. No. 13/842,463 filed Mar. 15, 2013 entitled "Diagnostic Simulator." The entire disclosures of those applications, including disclosures incorporated by reference therein, are incorporated by reference herein.

In various embodiments, phantoms described in the present disclosure simulate the optical and acoustic properties of a specific organ or tissue that make it possible to accurately simulate normal and abnormal tissues and the surrounding normal tissue. In an embodiment, the methods of the present disclosure for creating such phantoms comprise a number of simple steps that result in a high-quality standard that remains constant over time. In various embodiments, the compositions and methods of the present disclosure provide a phantom formulation where each individual component controls only a single physical property without noticeably affecting other relevant properties of the phantom. By varying the concentrations of the various components and parameters of the various steps or phases of the method, a large number of possible configurations may be simulated to match properties of different organs and tissues and different normal and pathological conditions.

In various embodiments, the present disclosure relates to compositions and methods for creating phantoms for medical imaging instrumentation, the phantoms comprising a first hydrogel matrix or other type of matrix containing additives for simulating the relevant optical and acoustic properties of a living organ or tissue. In an embodiment, additives may include:

absorbing molecules, ions or nanoparticles to adjust the absorptive properties of the matrix at either a single light wavelength, or a number of light wavelengths simultaneously;

nano- and microparticles with dimensions approximately ranging from 0.1-10 μm to adjust light scattering properties of the phantom that do not absorb light in specific visible and near-infrared wavelength ranges;

monodispersed or polydispersed microparticles (that also do not absorb light) with dimensions that appear in range 10-250 μm to adjust acoustic attenuation and ultrasound backscatter coefficient in the wide range of ultrasonic frequencies, surfactants for ensuring stability of all additives in solution during all stages of a phantom preparation process; and preservatives to prevent bacterial and fungal growth in the phantom and extend the phantom's lifetime.

Table 1 below provides an exemplary list of substances that can be components of a gelatin matrix that duplicates or closely resembles various properties of tissue in vivo.

centrations that can be used for modeling of biological tissues for optoacoustic imaging. The figures relate to the density, speed of sound, acoustic impedance, volumetric expansion coefficient, and absorption spectra of gelatin gels without additives. In the Figures, the concentrations of gelatin hydrogels are measured in a percentage that defines the mass fraction of gelatin relative to the total mass of the sample.

TABLE 1

Table of opto-acoustic properties and materials that modify a specific property of a gelatin matrix used to simulate a tissue in vivo.

| Property | Material | Concentration | Property range | Comments | Other materials |
|---|---|---|---|---|---|
| speed of sound at 22° C. c, mm/µs | Gelatin | 5-20% | 1.5-1.57 | Speed of sound should be corrected for different temperatures. | Other transparent hydrogels (e.g. PAA) or polymers (e.g. plastisol, silicone), etc. |
| Density ρ, g/cm³ | Gelatin | 5-20% | 1.0-1.06 | | |
| Acoustic impedance, MRayls | Gelatin | 5-20% | 1.50-1.66 | | |
| Ultrasound attenuation coefficient, dB/MHz/cm | Polyethylene microspheres, Ø 10-150 µm | 0-10 mg/ml | 0.5-3 | | Other types of micrometer-sized particles (microspheres made of other types of polymers, silica, glass, etc.) |
| Ultrasound backscatter coefficient, dB/MHz/cm | Polyethylene microspheres, Ø 10-150 µm | not measured | | | |
| Optical absorption, $\mu_a$, cm$^{-1}$ | carbon nanoparticles (carbon nanotubes, carbon black) suspended in appropriate surfactants, hemoglobin | 0.001-10 mg/ml | 0-5 | concentration depends on molar extinction coefficient of a particular absorber at a specific wavelength | organic dyes, gold and silver nanoparticles, ionic salt solutions (NiSO4, CuSo4), etc. |
| Reduced scattering coefficient at 757 nm $\mu_s'$, cm$^{-1}$ | TiO$_2$ | 0-5 mg/ml | 1-30 | Depends on particle size distribution | rare earth metal oxides microcrystals, silica and polymeric microspheres and nanospheres |
| Optical scattering anisotropy | TiO$_2$ | 0-5 mg/ml | 0.5-0.9 | Depends on particle size distribution | |
| Surfactant | CTAB | 1% | | Stabilizes suspensions of micro- and nano-particles in solution during phantom preparation | Other types of surfactants, sodium dodecyl sulfate, etc. |
| Antibacterial/ antifungal | Methyl parabene | 1 mg/ml | | | Other types of preservatives, ex. timerosal, colloidal silver, etc. |
| Antibacterial/ antifungal | Chlorhexidine digluconate | 0.15% | | | |

Note that Table 1 is intended to be illustrative, and not limiting. One skilled in the art of optical and acoustic properties can widen this list to all substances now known or later to be developed that can affect optical and acoustic properties of a gelatin matrix at given optical wavelengths and ultrasound frequencies.

Physical Properties of Gelatin-Based Hydrogels

FIGS. 1 to 5 illustrate an embodiment of physical properties of gelatin-based hydrogels with different gelatin con- FIG. 1A illustrates an embodiment of the density of gels as a function of gelatin concentration at 25° C. In the illustrated embodiment, density was measured directly as a mass to volume ratio, as well as calculated using data shown in FIG. 1B. FIG. 1B illustrates an embodiment of the coefficient of volumetric expansion in gelatin hydrogels relative to water volume used to dissolve a given quantity of gelatin.

Figure 2:
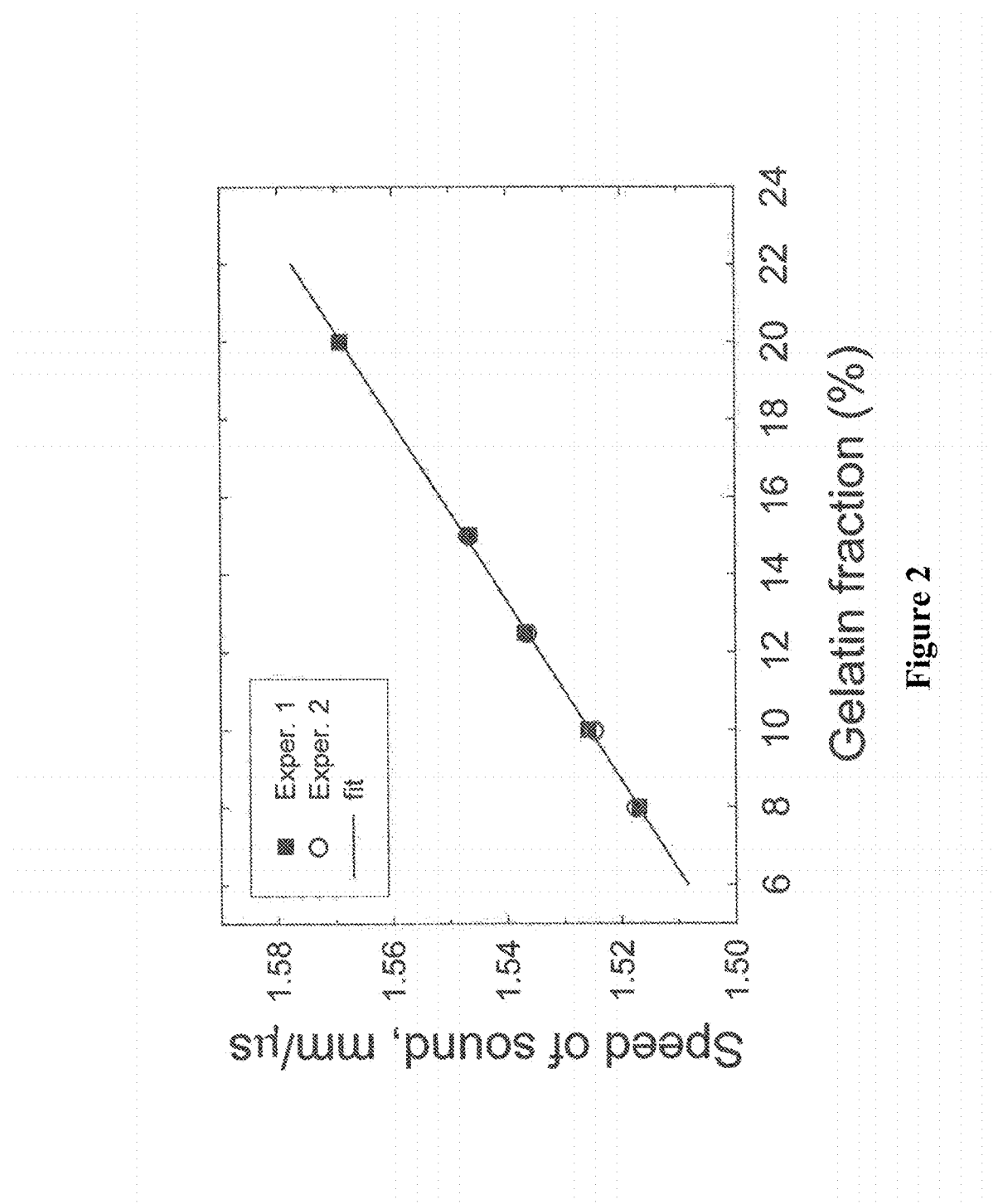
FIG. 2 illustrates an embodiment of the speed of sound in gelatin-based hydrogels as a function of gelatin density.

FIG. 2 illustrates an embodiment of the speed of sound in gelatin-based hydrogels as a function of gelatin density. In the illustrated embodiment, measurements were performed at 22° C.

Figure 3:
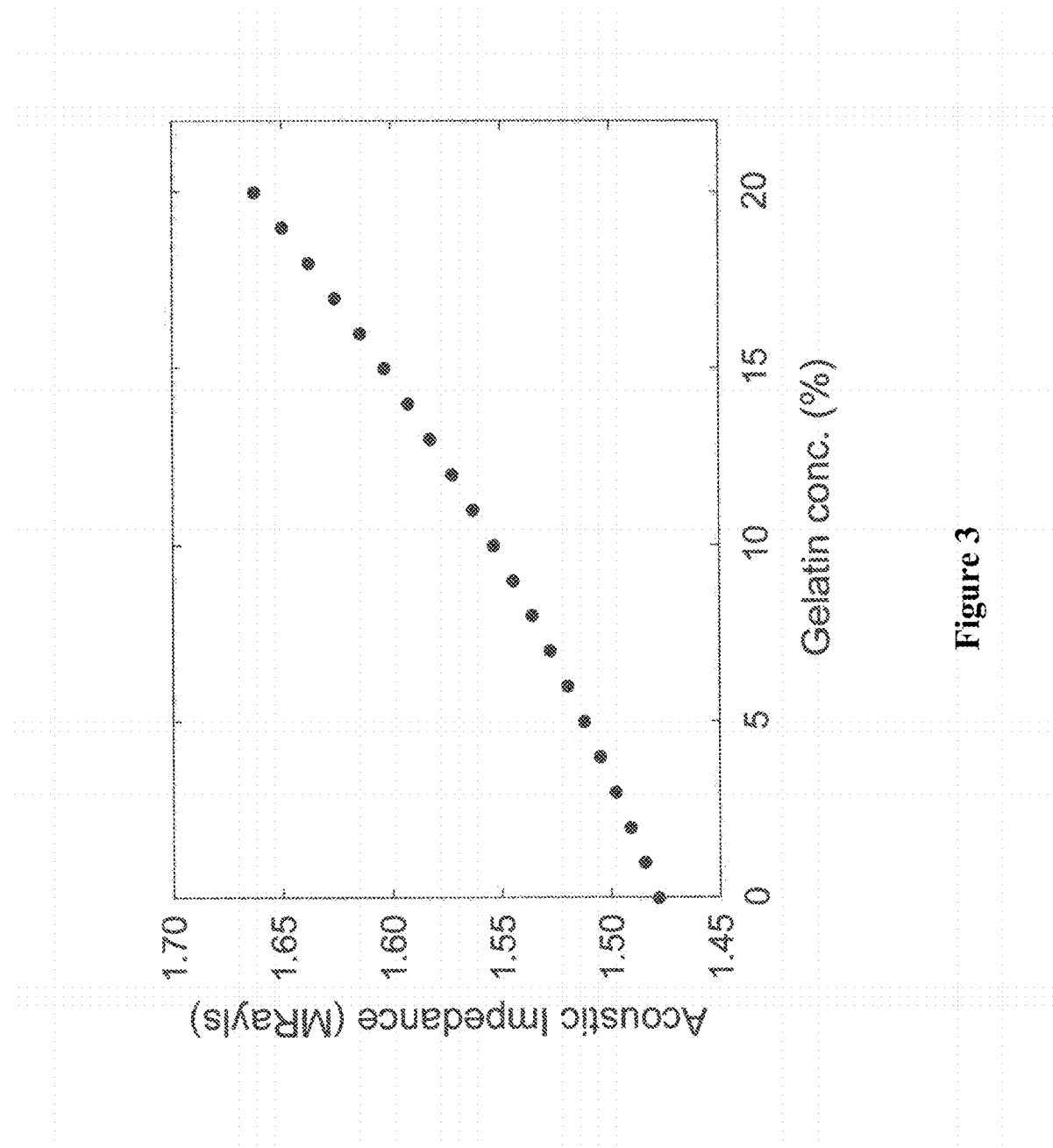
FIG. 3 illustrates an embodiment of the acoustic impedance of gelatin-based hydrogels given as a product of speed of sound and gel density.

FIG. 3 illustrates an embodiment of the acoustic impedance of gelatin-based hydrogels given as a product of speed of sound and gel density.

Figure 4A:
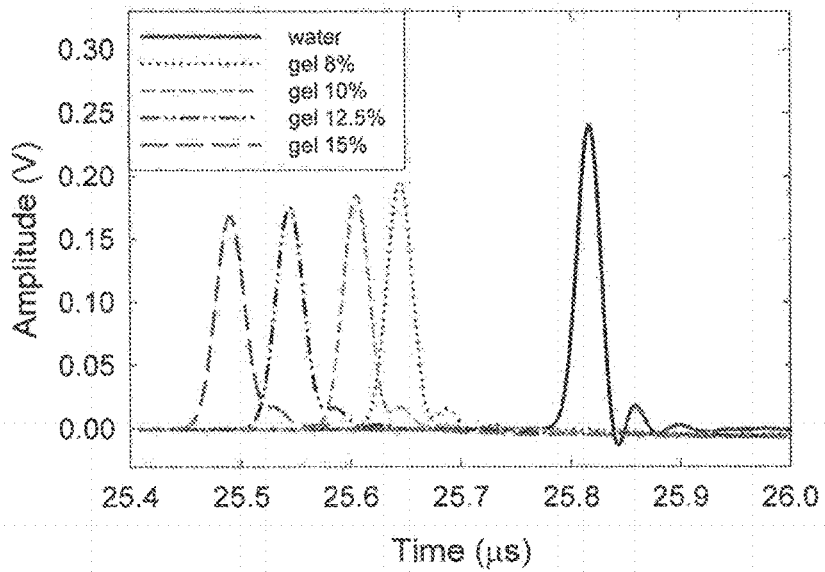
FIG. 4A illustrates an embodiment of recorded signals generated by a plane wave Δ-source after passing through gels of different densities.
Figure 4B:
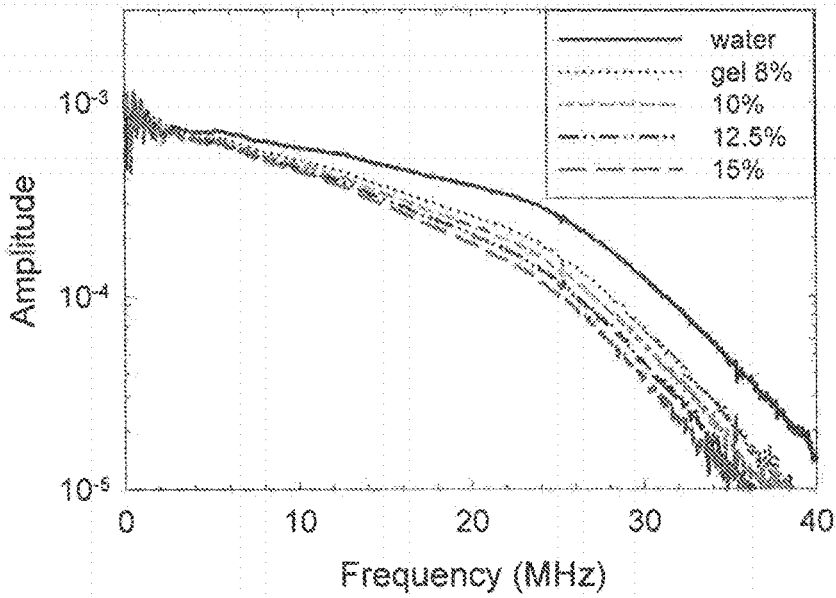
FIG. 4B illustrates an embodiment of the frequency spectra of the recorded signals of FIG. 4A.
Figure 4C:
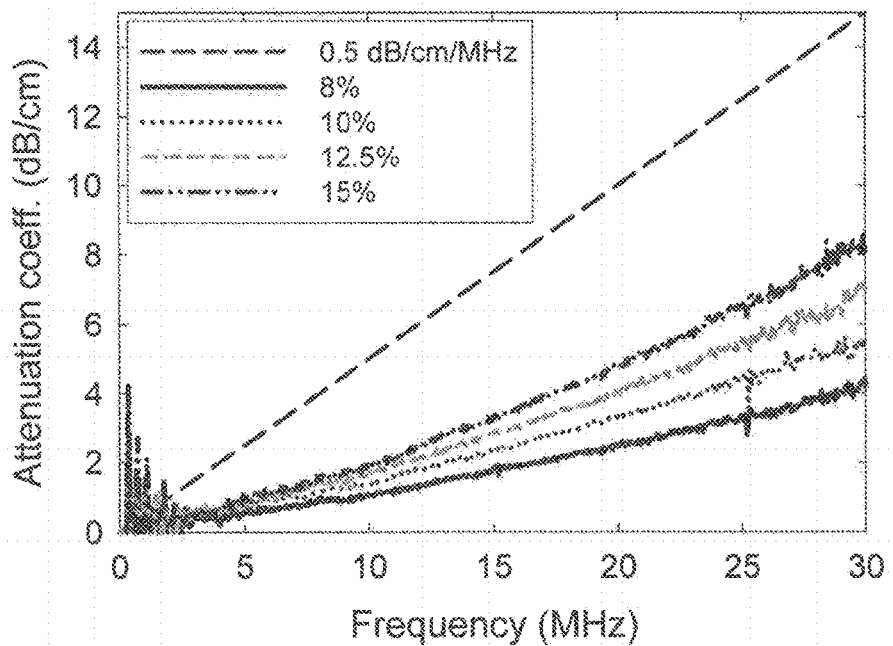
FIG. 4C illustrates an embodiment of frequency-dependent acoustic attenuation coefficients of gelatin samples calculated from data shown in FIG. 4C.

FIG. 4A illustrates an embodiment of recorded signals generated by a plane wave Δ-source after passing through gels of different densities. FIG. 4B illustrates an embodiment of the frequency spectra of the recorded signals of FIG. 4A. FIG. 4C illustrates an embodiment of frequency-dependent acoustic attenuation coefficients of gelatin samples calculated from data shown in FIG. 4C.

Figure 5A:
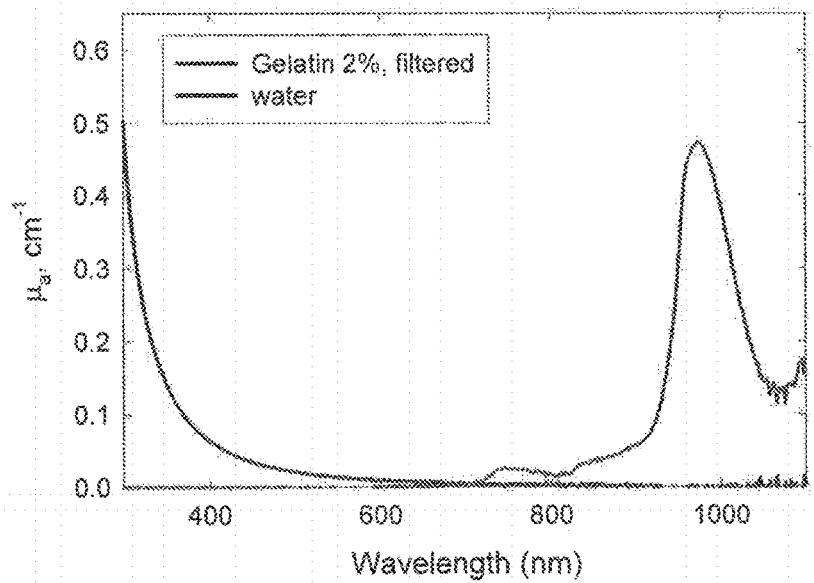
FIG. 5A illustrates an embodiment of the absorption spectra of the pure water and a 2% gelatin gel measured against a water background.
Figure 5B:
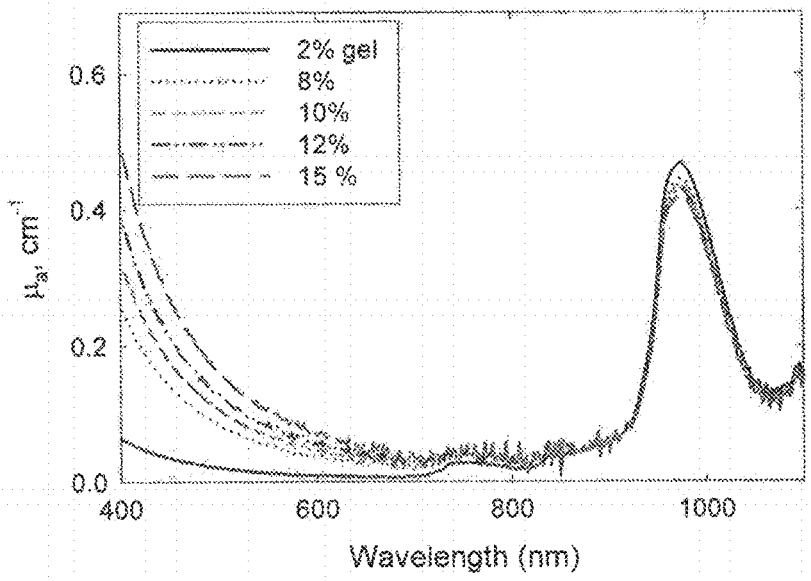
FIG. 5B illustrates an embodiment of the absorption spectra of gels with different gelatin concentrations deduced using data from FIGS. 5A and 1B.

FIG. 5A illustrates an embodiment of the absorption spectra of the pure water and a 2% gelatin gel measured against water background. In the illustrated embodiment, after dissolving gelatin, the solution was filtered through 0.22 μm filter to remove scattering impurities. FIG. 5B illustrates an embodiment of the absorption spectra of gels with different gelatin concentrations deduced using data from FIGS. 5A and 1B.

Modeling Optical Properties of Tissues in Gelatin-Based Hydrogels

In various embodiments, an optoacoustic phantom mimics the optical properties of tissues in order to accurately reproduce light distribution in real samples. The physical parameters that define light transport in a scattering medium include scattering coefficient $\mu_s$ (probability of photon scattering per unit of length), absorptivity coefficient $\mu_a$ (probability of photon absorption per unit of length), and dimensionless optical anisotropy factor g that defines an average cosine of a photon scattering angle. The most relevant parameter is the light attenuation coefficient $\mu_{eff}$, that defines the intensity of light I at a given depth h in a scattering medium in case of a uniform surface illumination:

$$I = I_0 \exp(-\mu_{eff} \cdot h)$$

$$\mu_{eff} = \sqrt{3\mu_a(\mu_a + \mu'_s)}$$

$$\mu'_s = \mu_s(1-g) \quad \text{(Equation 1)}$$

The parameter $\mu'_s$ is the reduced scattering coefficient. From equation 1 it follows that reduced scattering and absorption coefficients $\mu'_s$ and $\mu_a$ are adjusted in a phantom in order to adequately replicate the penetration of light into a live tissue. For example, Table 2 illustrates an embodiment of optical properties of breast tissue.

TABLE 2

Summary of optical properties of human breast tissues *.

| Breast tissue type | Wavelength, nm | $\mu_a$, cm$^{-1}$ | $\mu'_s$, cm$^{-1}$ | g |
|---|---|---|---|---|
| Fatty tissue | 749 | | 8.5 ± 3.5 | |
| Fatty tissue | 700 | | 13 ± 5 | 0.95 |
| Fibroglandular tissue | 700 | | 12 ± 5 | 0.92 |
| breast, in vivo | 800 | | 7.2-13.5 | |
| Fatty tissue | 789 | 0.08 ± 0.1 | 7.7 ± 2.6 | |
| Fibrous tissue | 789 | 0.06 ± 0.12 | 8.9 ± 2.5 | |

* Vo-Dinh, T., Biomedical Photonics Handbook; CRC Press, 2003.

In various embodiments, in optical tissue phantoms light scattering is mediated by microparticles that do not contribute to absorption and only scatter photons, that is to say, these particles do not affect acoustic properties of the phantom, i.e. change its speed of sound, density, and acoustic attenuation coefficient. In at least some of the embodiments discussed below, titanium dioxide (TiO$_2$) microcrystals that do not absorb light with wavelengths above 450 nm are used. It should be understood, however, that those skilled in the art will readily appreciate that other micro- and nano-particles satisfy the aforementioned criteria and may be used to adjust light scattering properties in phantoms.

FIG. 6A-D illustrates an embodiment of the measured $\mu'_s$ and g parameters of TiO$_2$ microparticles (Sigma Aldrich, Titanium(VI) oxide, extra pure, part number 14027) suspended in aqueous solution of 1% cetyltrimethylammonium bromide (CTAB). In the illustrated embodiment, the surfactant CTAB is used, inter alia, to stabilize TiO$_2$ microparticles in solution and prevent aggregation.

Figure 6A:
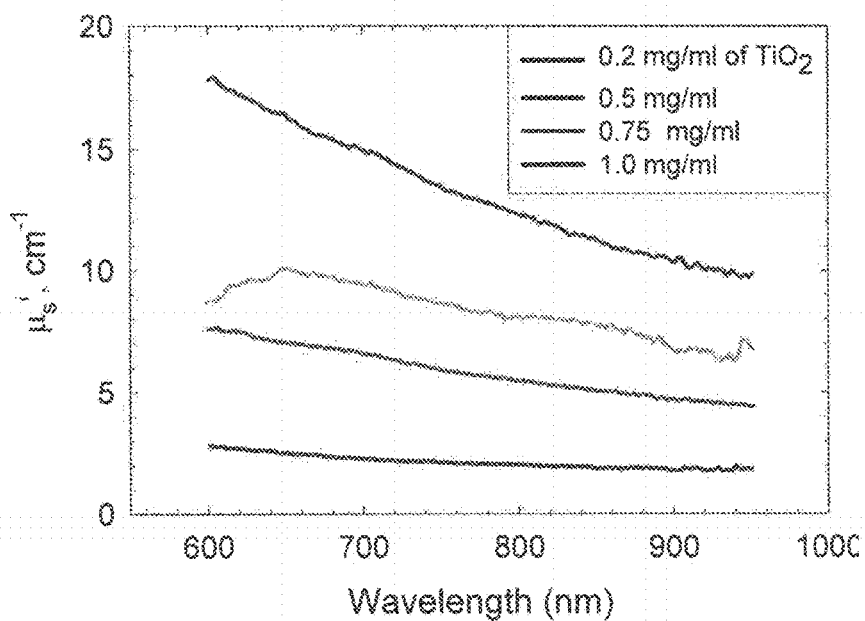
FIG. 6A illustrates an embodiment of the reduced scattering coefficient $\mu'_s$ in solutions containing different concentrations of $TiO_2$ microparticles suspended in 1% CTAB/water mixture.
Figure 6B:
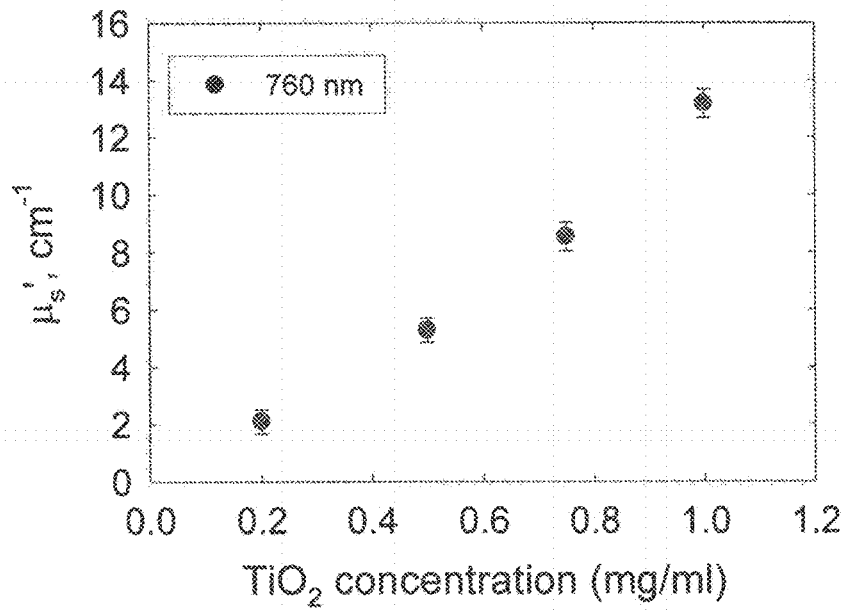
FIG. 6B illustrates an embodiment of optical anisotropy factor g of solutions containing different concentrations of $TiO_2$ microparticles suspended in 1% CTAB/water mixture.
Figure 6C:
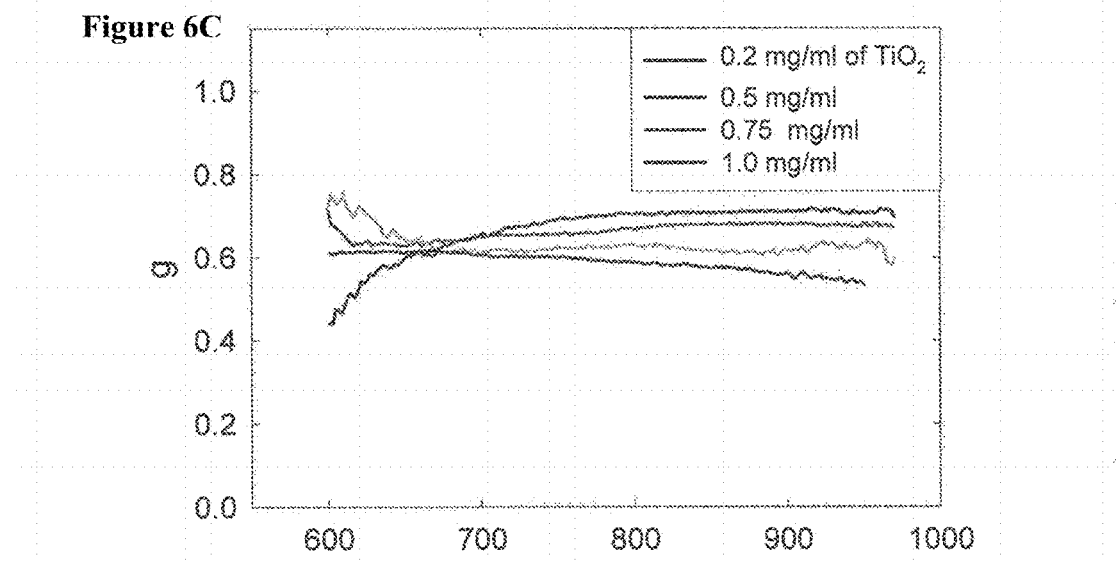
FIG. 6C illustrates an embodiment of the reduced scattering coefficient $\mu'_s$ at 760 nm in solutions containing different concentrations of $TiO_2$ microparticles suspended in 1% CTAB/water mixture.
Figure 6D:
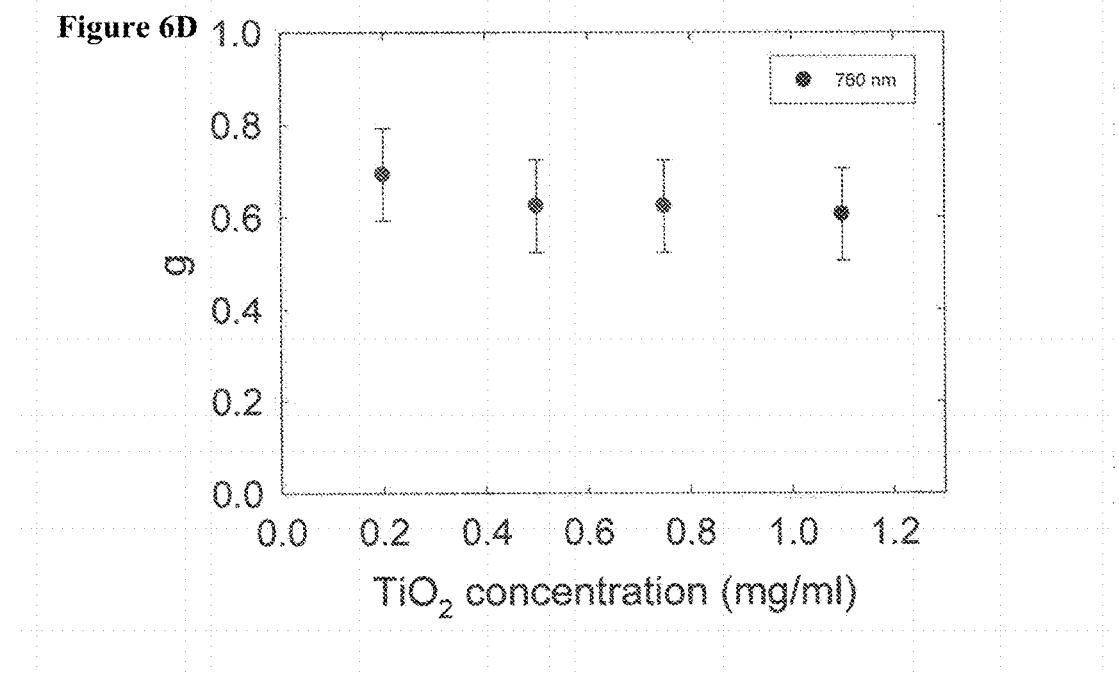
FIG. 6D illustrates an embodiment of the optical anisotropy factor g at 760 nm at 760 nm in solutions containing different concentrations of $TiO_2$ microparticles suspended in 1% CTAB/water mixture.

FIG. 6A illustrates an embodiment of the reduced scattering coefficient $\mu'_s$ in solutions containing different concentrations of TiO$_2$ microparticles suspended in 1% CTAB/water mixture. FIG. 6B illustrates an embodiment of optical anisotropy factor g of solutions containing different concentrations of TiO$_2$ microparticles suspended in 1% CTAB/water mixture. FIG. 6C illustrates an embodiment of the reduced scattering coefficient $\mu'_s$ at 760 nm in solutions containing different concentrations of TiO$_2$ microparticles suspended in 1% CTAB/water mixture. FIG. 6D illustrates an embodiment of the optical anisotropy factor g at 760 nm at 760 nm in solutions containing different concentrations of TiO$_2$ microparticles suspended in 1% CTAB/water mixture. In the illustrated embodiments, it can be seen that the reduced scattering coefficient $\mu'_s$ gradually increases as the TiO2 concentration increases, while optical anisotropy factor g remains approximately the same.

FIG. 7-10 illustrates how, in an embodiment, TiO$_2$ changes only $\mu'_s$ and g in gelatin samples and does not affect other physical properties of the phantom.

Figure 7A:
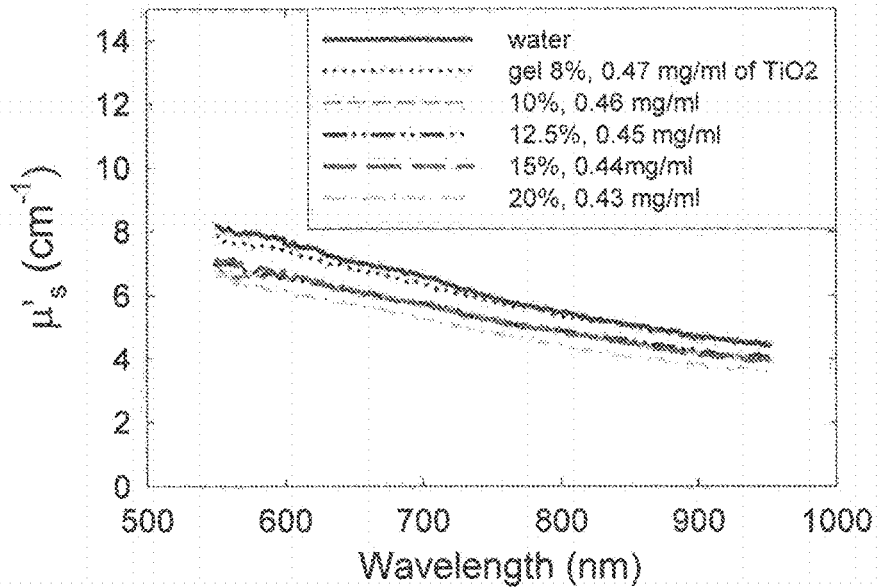
FIG. 7A illustrates an embodiment of measured scattering coefficient $\mu'_s$ values in samples of water and gelatin-based hydrogels containing approximately similar concentrations of TiO2 microparticles.
Figure 7B:
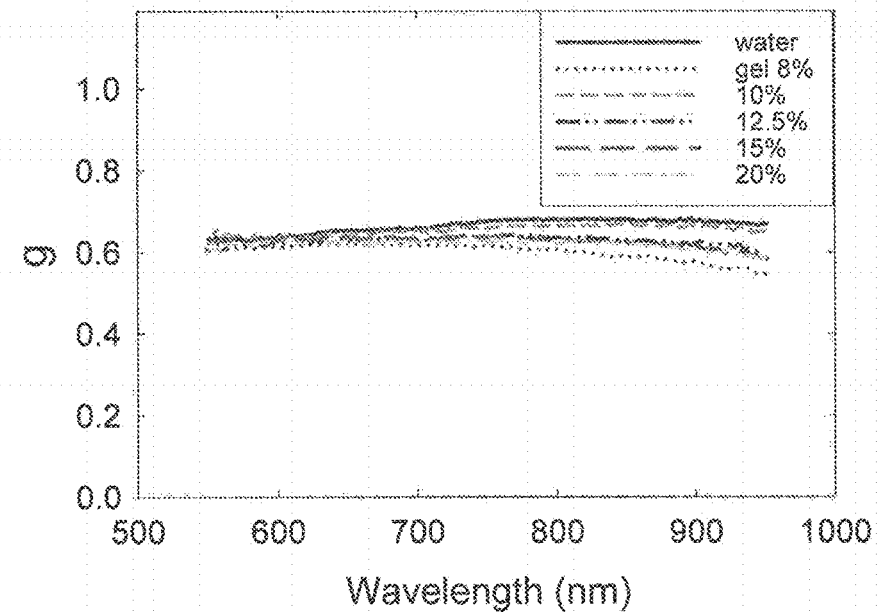
FIG. 7B illustrates an embodiment of optical anisotropy factor g in samples of water and gelatin-based hydrogels containing approximately similar concentrations of TiO2 microparticles.
Figure 7C:
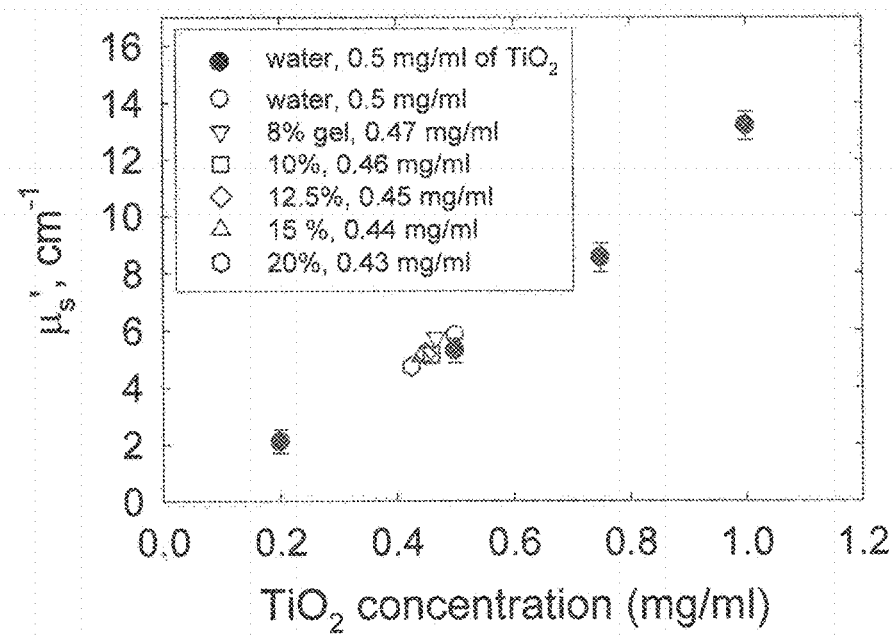
FIG. 7C illustrates an embodiment of a comparison of measured scattering coefficient $\mu'_s$ values in gels with those measured in aqueous suspension of $TiO_2$ microparticles in CTAB at 760 nm.

FIG. 7A illustrates an embodiment of the reduced scattering coefficient $\mu'_s$ values in samples of water and gelatin-based hydrogels containing approximately similar concentrations of TiO2 microparticles. FIG. 7B illustrates an embodiment of the optical anisotropy factor g in samples of water and gelatin-based hydrogels containing approximately similar concentrations of TiO2 microparticles. FIG. 7C illustrates an embodiment of a comparison of reduced scattering coefficient $\mu'_s$ values in gels with those measured in aqueous suspension of TiO$_2$ microparticles in CTAB at 760 nm. It can be seen in FIG. 7A-C, inter alia, that gelatin samples of different densities with added TiO$_2$ microparticles have identical $\mu'_s$ and g values as the aqueous suspensions of TiO$_2$ in CTAB shown in FIG. 6.

Figure 8:
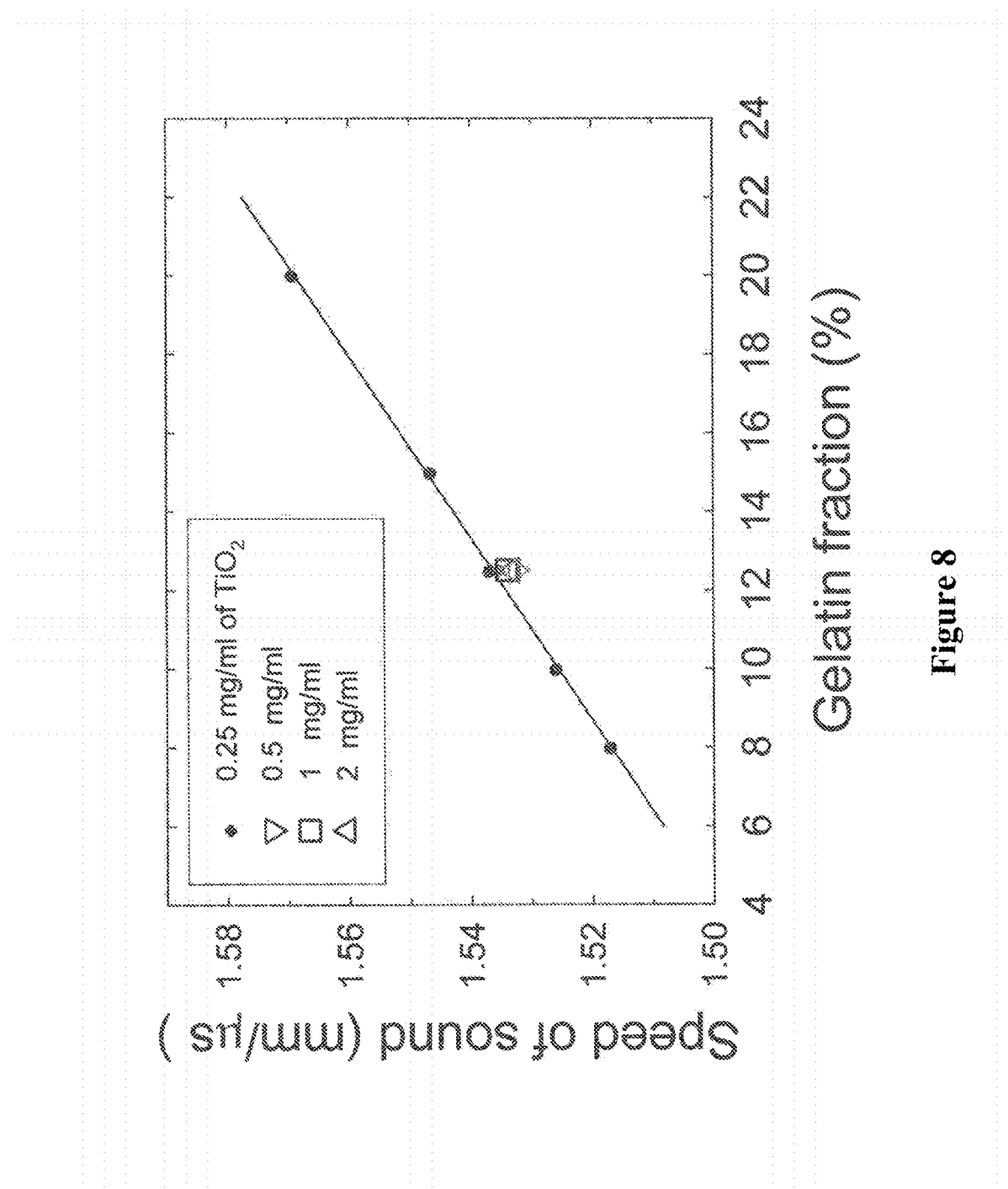
FIG. 8 illustrates an embodiment of the speed of sound in 12.5% gelatin samples at 22° C. containing different concentrations of $TiO_2$.

FIG. 8 illustrates an embodiment of the speed of sound in 12.5% gelatin samples at 22° C. containing different concentrations of TiO$_2$. FIG. 8 demonstrates, inter alia, that the speed of sound in gelatin samples that contain 0.25-2 mg/ml of TiO$_2$ microparticles remains nearly identical to that of pure gelatin hydrogels.

Figure 9A:
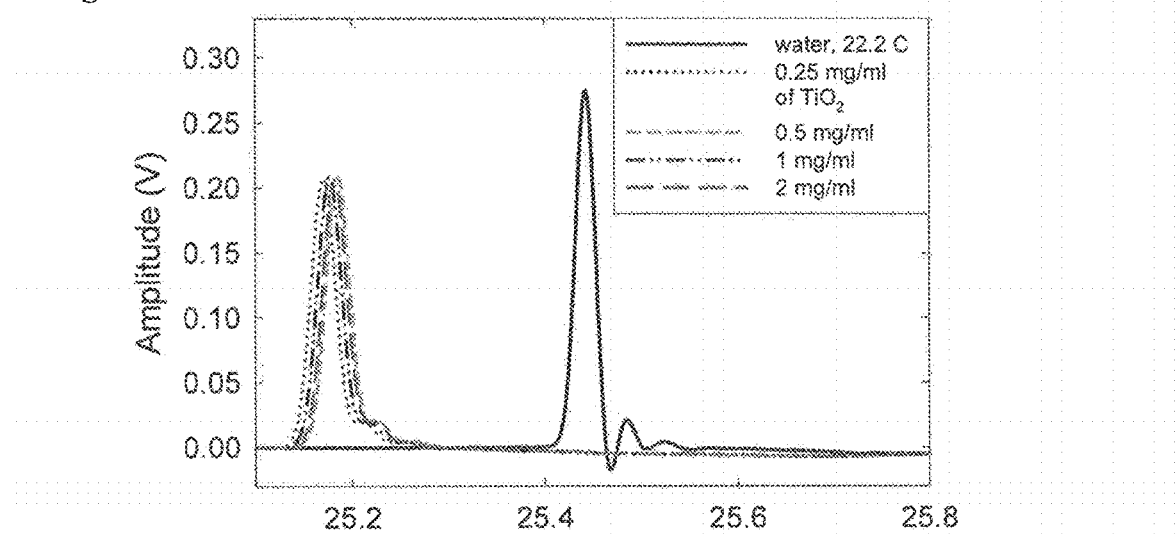
FIG. 9A illustrates an embodiment of recorded signals generated by a plane wave Δ-source after passing through gels of different densities.
Figure 9B:
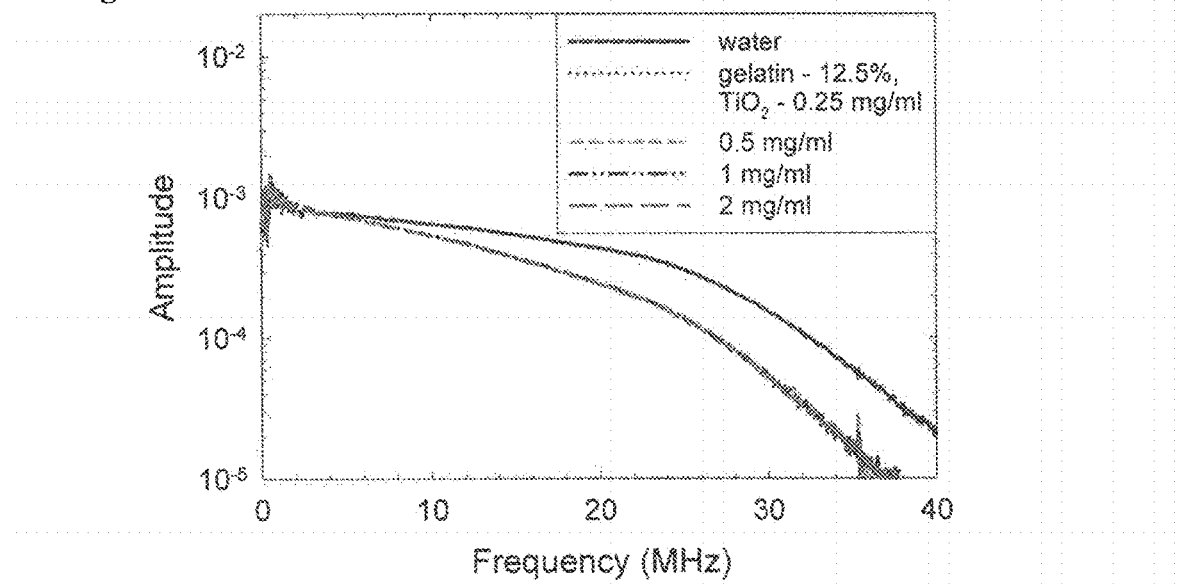
FIG. 9B illustrates an embodiment of the frequency spectra of the recorder signals in FIG. 9A.
Figure 9C:
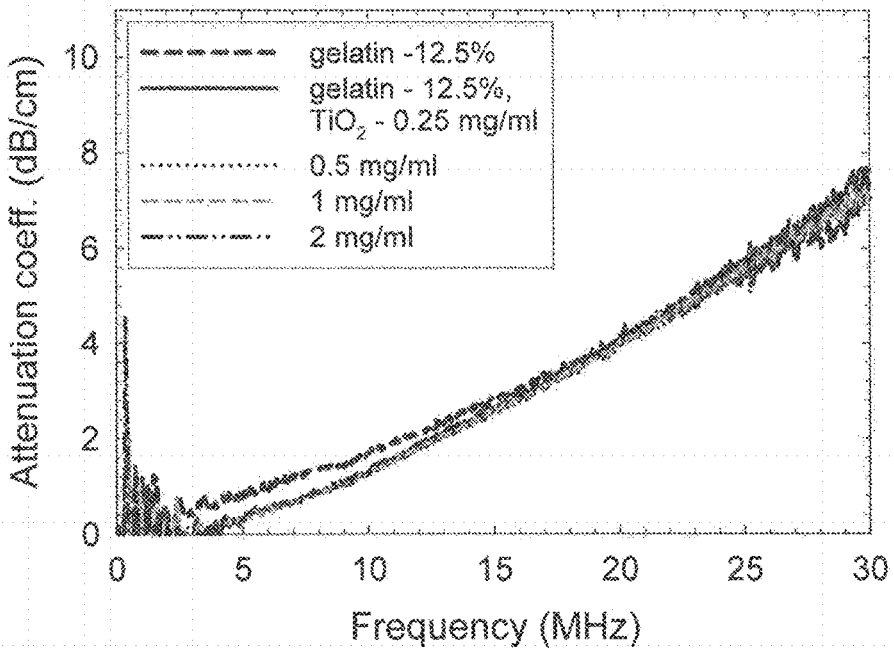
FIG. 9C illustrates an embodiment of frequency-dependent acoustic attenuation coefficients of gelatin samples with $TiO_2$ calculated from data shown in FIG. 9B.

FIG. 9A illustrates an embodiment of recorded signals generated by a plane wave Δ-source after passing through gels of different densities. FIG. 9B illustrates an embodiment of the frequency spectra of the recorder signals in FIG. 9A. FIG. 9C illustrates an embodiment of frequency-dependent acoustic attenuation coefficients of gelatin samples with TiO$_2$ calculated from data shown in FIG. 9B. FIG. 9 shows that, inter alia, the acoustic attenuation coefficient in these samples remains identical to that of pure gelatin gel of a given density. In an embodiment, the absorptivity coefficient $\mu_a$ at the desired wavelength can be adjusted by adding additional absorbers to the gelatin matrix.

Figure 10:
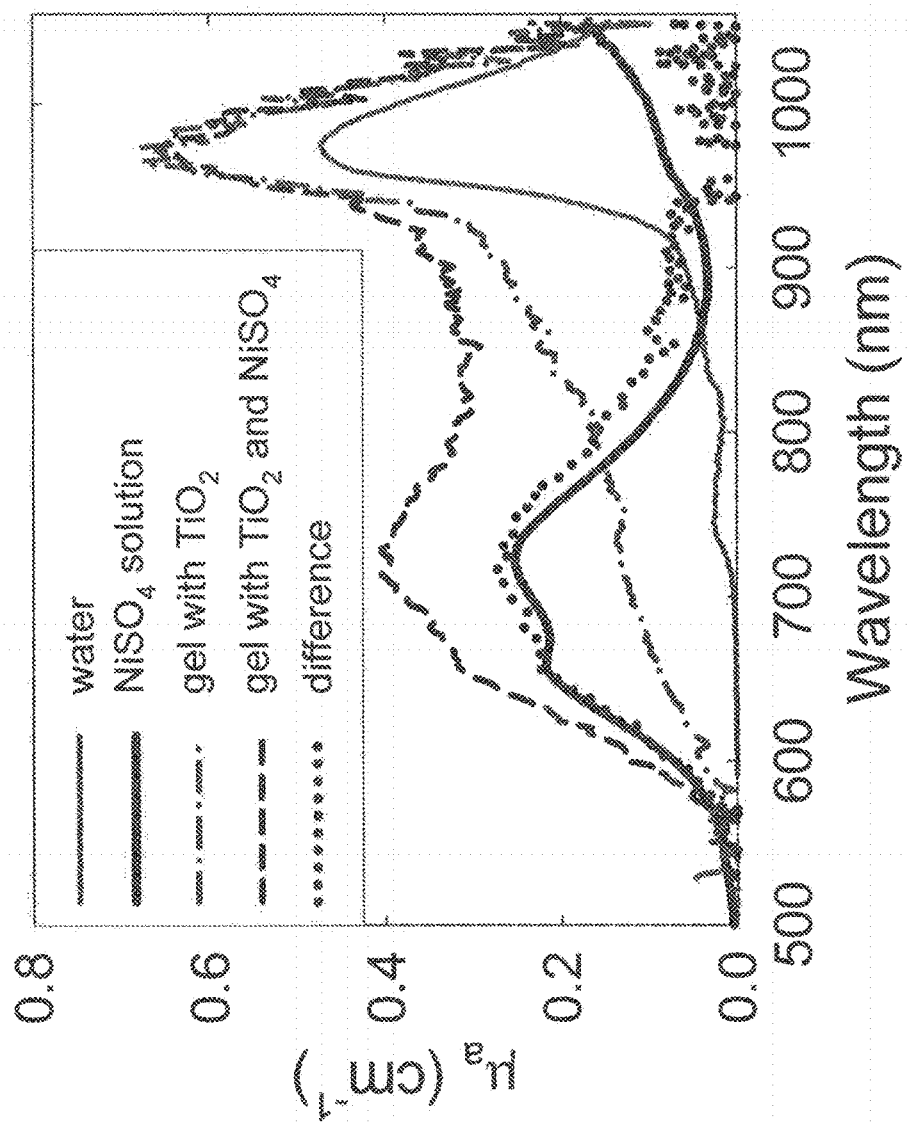
FIG. 10 illustrates an embodiment of adjusting absorption background of a gelatin matrix.

FIG. 10 illustrates an embodiment of adjusting absorption background of a gelatin matrix. The solid lines show the measured absorption spectra of an optically clear sample of water and an $NiSO_4$ aqueous solution. The dashed lines show the absorption spectra of 10% gelatins, one including $NiSO_4$, one not, and each containing 0.5 mg/ml of TiO2 (obtained with inverse adding-doubling algorithm). The dotted line shows the difference between these spectra, that matches the absorption spectrum of the solution. In the illustrated embodiment, the small systematic error of ≤0.2 cm−1 in the calculated absorption spectra is likely arises from varying reflectivity of the integrating sphere wall in the measured wavelength range FIG. 10 shows, inter alia, how the addition of an dyed solution changes the absorptivity coefficient $\mu_a$ of a gel matrix. In the illustrated embodiments, as the size of individual absorbing particles is significantly less than the wavelength of the light used, and thus will not affect in any significant way light scattering or acoustic properties of a phantom utilizing such gels.

Modeling Acoustic Properties of Tissues in Gelatin-Based Hydrogels

In various embodiments, gelatin hydrogels have very similar speed of sound and acoustic impedance values as compared to those of real tissues. See Table 3 below. Thus, in an embodiment, only acoustic attenuation coefficient of a gel matrix utilized in a phantom needs to be adjusted, since the slope a of frequency-dependent acoustic attenuation coefficient in gelatin hydrogels appear to be less than 0.25 dB/(cm MHz). The American Institute of Ultrasound in Medicine (AIUM) Technical standards committee recommends that a appears in the range 0.3-0.7 dB/cm/MHz in ultrasound phantom materials.

ticles and different concentrations polyethylene microspheres. FIG. 13C illustrates an embodiment of a comparison of reduced scattering coefficient $\mu'_s$ values in gels with those measured in aqueous suspension of TiO2 microparticles in CTAB at 760 nm.

Figure 12:
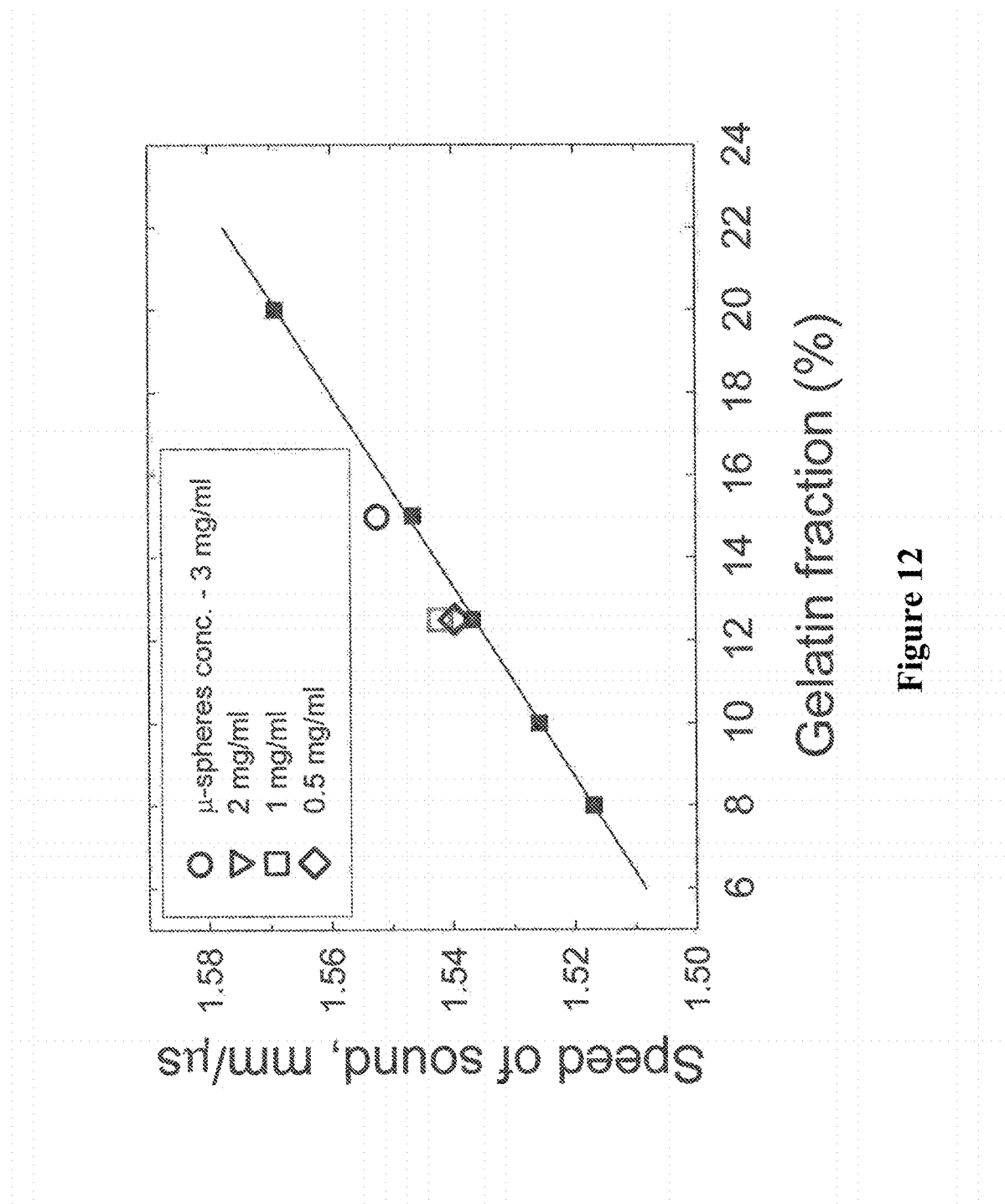
FIG. 12 illustrates an embodiment of speed of sound measurements of gelatin hydrogels containing different concentrations of polyethylene microspheres.

FIGS. 12 and 13 show that, inter alia, the speed of sound, optical anisotropy and the reduced scattering coefficients remain nearly the same in these samples. Thus, in various embodiments, additives on the scale of several mg/ml will not noticeably affect the density of the samples. In the illustrated embodiments, the absorptivity coefficient $\mu_a$ of the samples is not significantly affected since polyethylene in the microspheres does not absorb light in the visible and near-infrared wavelength range.

Phantom Design for Calibration of Optoacoustic/Ultrasound Imaging Instrumentation Using the methods and compositions described above, opto-acoustic phantoms designed for calibration, testing and validation of medical imaging and sensing modalities can be constructed.

In various embodiments, such phantoms can be constructed to accurately replicate optical tissue properties within near-infrared spectral range from 650 nm to 1250 nm and acoustic properties of biological tissues in the ultrasonic frequency range from 100 kHz to 20 MHz, i.e. the ranges that correspond to operation parameters of medical imaging and sensing modalities. In an embodiment, such optical properties include one or more of the absorptivity coefficient $\mu_a$, the reduced scattering coefficient $\mu'_s$ and the optical anisotropy factor g of the phantom and its components. In an embodiment, such acoustic properties include one or more of speed of sound, density, acoustic attenuation and acoustic

TABLE 3

Summary of Acoustic Properties of Human Breast Tissues.

| | Speed of sound, mm/µs | Density, g/cm³ | Acoustic impedance, MRayls | Acoustic attenuation coefficient α, dB/(cm MHz) | Source |
|---|---|---|---|---|---|
| Human breast tissue | 1.43-1.57 | 0.99-1.06 | 1.42-1.66 | 1.3-1.8 | Duck, 1990 |
| Human skin | 1.54 | 1.11-1.19 | 1.71-1.83 | 1.4-2.3 | Duck, 1990 |
| Human breast tissue | 1.51 | 1.02 | 1.54 | 0.75 | ICRU, 1998 |
| Human soft tissue average | 1.56 | 1.04 | 0.54 | 1.63 | Mast, 2000 |

In at least some of the embodiments disclosed herein, polyethylene microspheres are used as additives to selectively adjust the acoustic attenuation coefficients of a gel matrix that could be used in a phantom.

Figure 11:
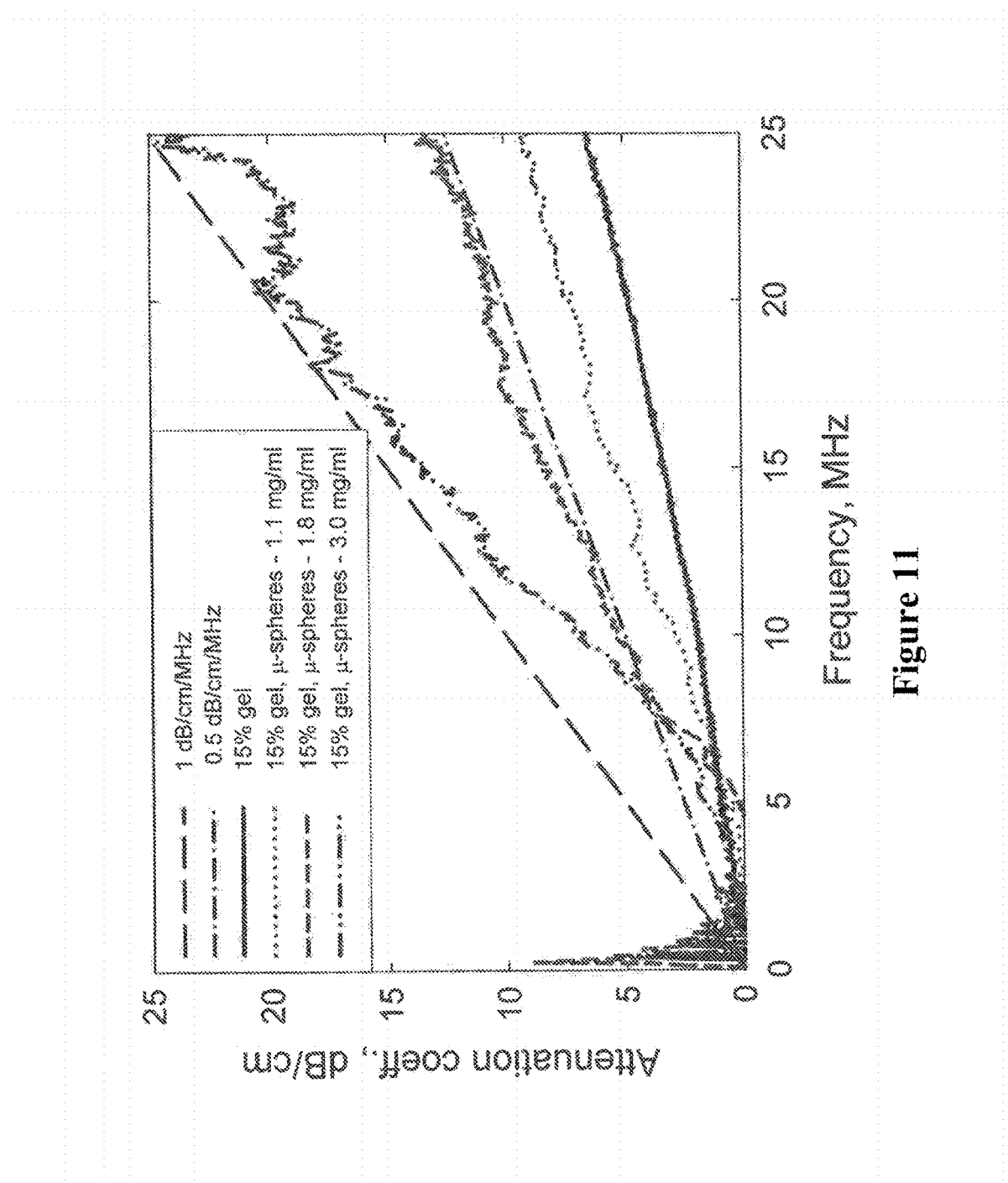
FIG. 11 illustrates an embodiment of the acoustic attenuation of gelatin hydrogels with different concentrations of polydisperse polyethylene microspheres with diameters ranging from 10 to 150 μm.

FIG. 11 illustrates an embodiment of the acoustic attenuation of gelatin hydrogels with different concentrations of polydisperse polyethylene microspheres with diameters ranging from 10 to 150 µm. FIG. 11 shows that, inter alia, increasing the concentrations of microspheres in the sample increases the ultrasound attenuation.

FIG. 12 illustrates an embodiment of speed of sound measurements of gelatin hydrogels containing different concentrations of polyethylene microspheres. The speed of sound in gelatin samples without additives (filled black squares) is shown for comparison.

Figure 13A:
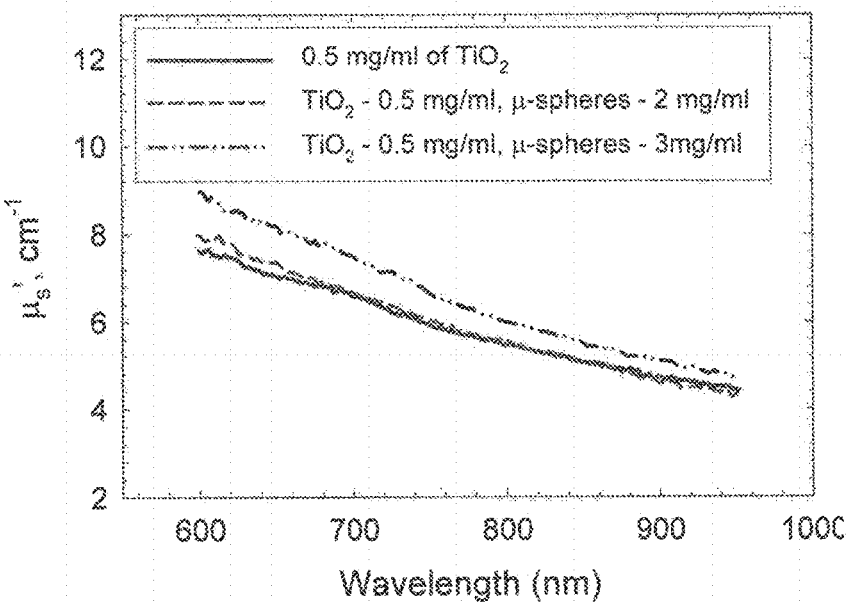
FIG. 13A illustrates an embodiment of scattering coefficients $\mu'_s$ values in 12.5% gelatin samples containing 0.5 mg/ml of $TiO_2$ microparticles and different concentrations polyethylene microspheres.
Figure 13B:
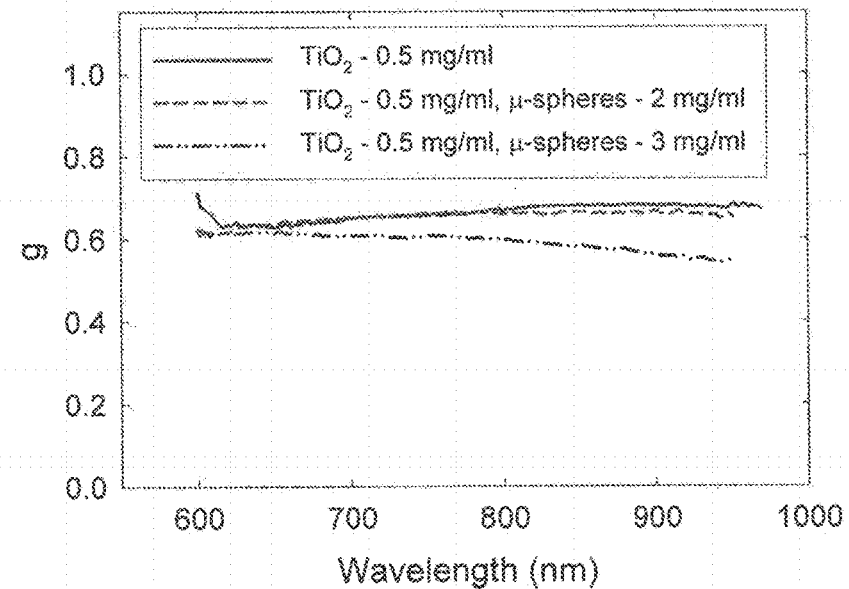
FIG. 13B illustrates an embodiment of the optical anisotropy factor g in 12.5% gelatin samples containing 0.5 mg/ml of TiO2 microparticles and different concentrations of polyethylene microspheres.
Figure 13C:
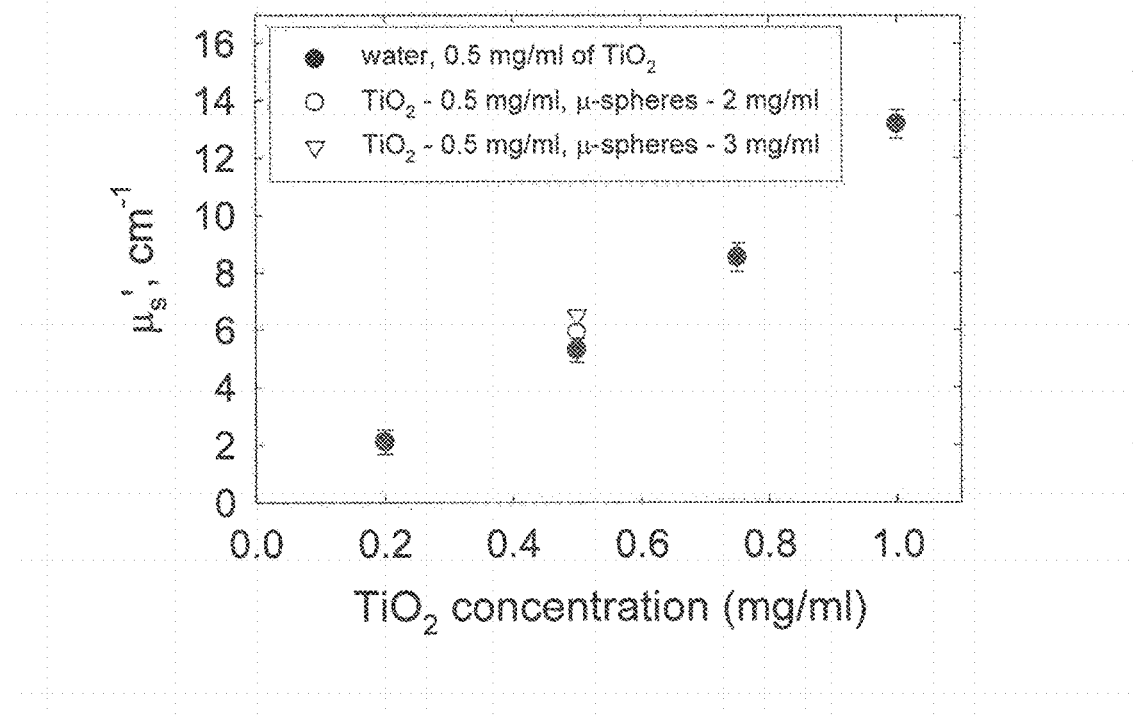
FIG. 13C illustrates an embodiment of a comparison of scattering coefficients $\mu'_s$ values in gels with those measured in aqueous suspension of TiO2 microparticles in CTAB at 760 nm.

FIG. 13A illustrates an embodiment of reduced scattering coefficient $\mu'_s$ values in 12.5% gelatin samples containing 0.5 mg/ml of $TiO_2$ microparticles and different concentrations polyethylene microspheres. FIG. 13B illustrates an embodiment of the optical anisotropy factor g in 12.5% gelatin samples containing 0.5 mg/ml of TiO2 microparbackscattering of the phantom and its component. Such phantoms can be fabricated using one or more background matrices representing tissue layers, where said matrices are made of hydrogel with predefined proportion of gelatin to water matching specific tissues of background with additives designed to match independently each optical and each acoustic properties of such matrices to optical and acoustic properties of background tissues;

one or more inclusion matrices made of hydrogel with predefined proportion of gelatin to water matching tissues of specific inclusions with additives designed to match independently each optical and each acoustic properties of inclusions that match morphology and functional properties of said tissues;

assembled and composed to protect the phantom properties for extended period of time without degradation or alteration.

In various embodiments, phantoms constructed using the compositions and methods of the present disclosure could comprise:

a hydrogel based on gelatin;
a number of background matrices are used to mimick properties of a layered tissue or otherwise complex inhomogeneous tissue, where such matrices possess shapes and properties formulated to match properties of layered and complex tissue structures;
layers may represent skin as a whole or skin epidermis and dermis, layer of fat, layer of muscles and aqueous layers;
a background matrix that mimics tissue that is macrohomogeneous but microheterogeneous and where microheterogeneities are represented by microspheres made of polyethelene of various densities and other microobjects made of materials having optical and acoustic properties of biological cells;
inclusions formulated to match optical and acoustic properties of malignant and benign tumors and blood vessels with properties of arteries and veins;
molecules, nanoparticles and microparticles used to accurately mimic optical properties of tissue in predetermined range of optical illumination wavelengths: including carbon, gold, silver, organic dyes, titanium dioxide, barium sulfate;
materials are used to accurately mimic acoustic properties of tissue in predetermined range of ultrasonic frequencies, including polystyrene microspheres of different sizes, gelatin of different
a case of protective material having at least one surface optically and acoustically transparent and accessible to imaging and sensing probes;
inclusions encased in thin polymer membranes or comprised of microparticles and nanoparticles not capable of diffusion out of such inclusions, thereby preserving optical and acoustic properties of inclusions.

Figure 14:
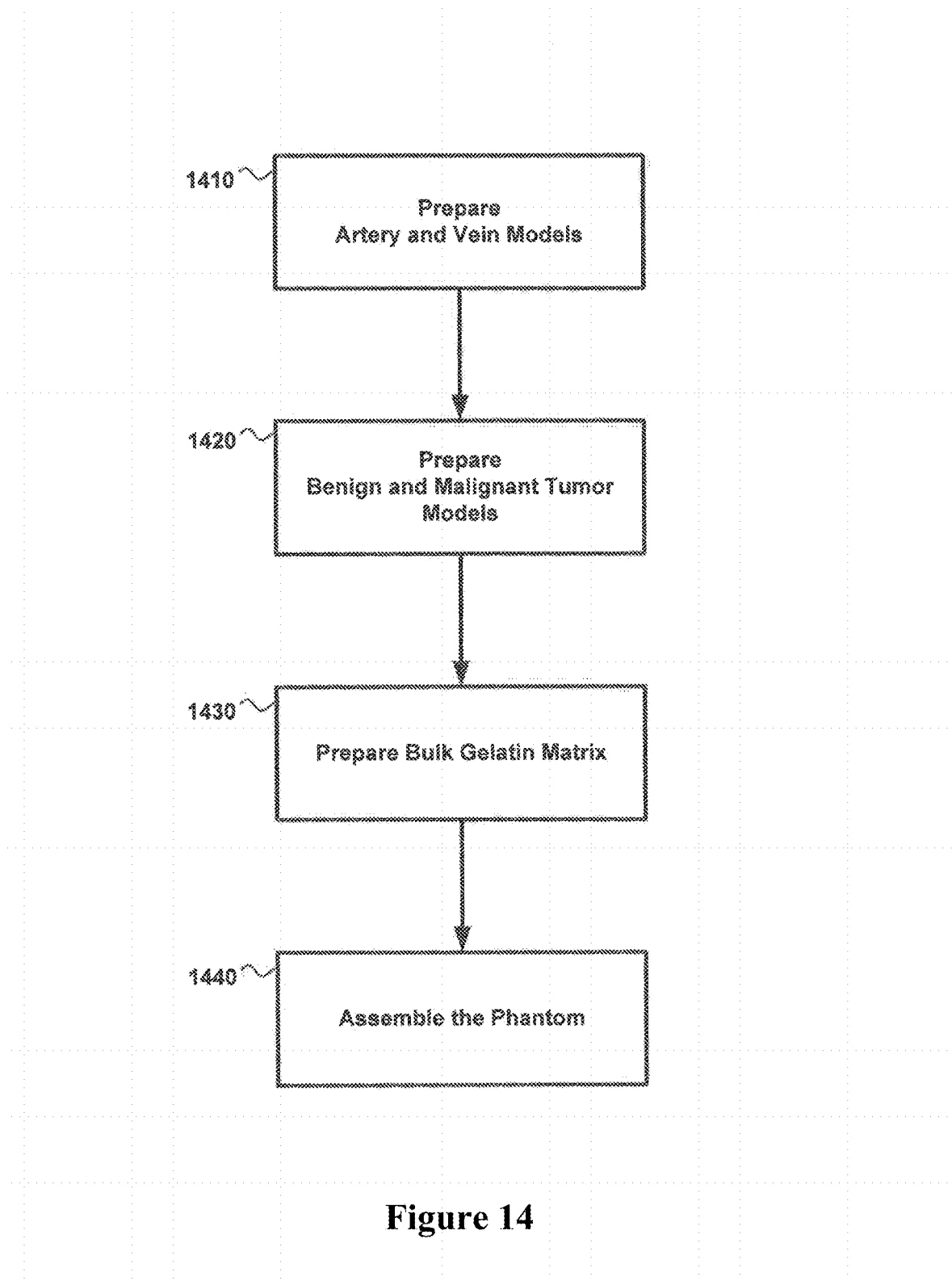
FIG. 14 illustrates an exemplary process for making a phantom that includes models of an artery and a vein, as well as models of benign and malignant tumors.

FIG. 14 illustrates an exemplary process for making a phantom that includes models of an artery and a vein, as well as models of benign and malignant tumors with different $\mu_a$ values at 757 and 1064 nm. It should be understood that the methodology described below is purely exemplary, and that other models could be constructed utilizing the compositions, materials and methods disclosed herein.

Figure 15:
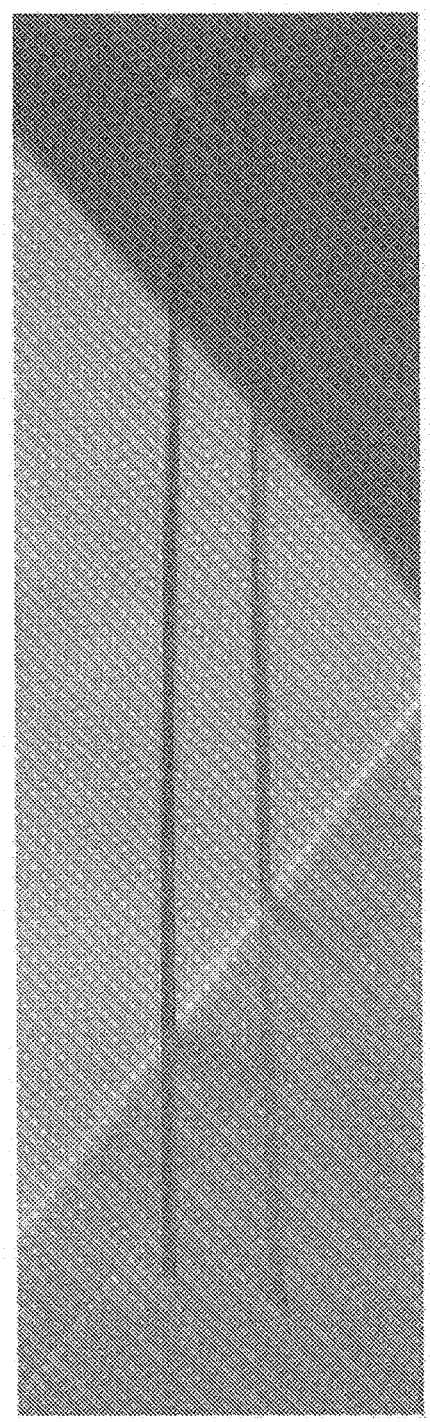
FIG. 15 illustrates an embodiment of artery and vein models prepared in the form of polyethylene tubes filled with gels.

In operation, 1410 of the method, artery and vein models are prepared. FIG. 15 illustrates an embodiment of artery and vein models prepared in the form of polyethylene tubes filled with gels. In an embodiment, such gels are used to immobilize nanoparticle-based absorbers to prevent their aggregation. In an embodiment, only the absorptivity coefficient $\mu_a$ of the gel matrix used to construct the artery and vein models is adjusted at specific wavelengths to model arteries and veins in vivo. Table 4 below illustrates targeted properties for exemplary vein and artery models.

TABLE 4

Target absorptivity coefficients of artery and vein models at two wavelengths.

| Wavelength | Hb, 40% HCT $\mu_a$, cm$^{-1}$ | HbO$_2$, 40% HCT $\mu_a$, cm$^{-1}$ | Artery model, 100% O$_2$ $\mu_a$, cm$^{-1}$ | Vein model, 70% O$_2$ $\mu_a$, cm$^{-1}$ |
|---|---|---|---|---|
| 757 nm | 8.32 | 3.1 | 4 | 4.7 |
| 1064 nm | 0.4 | 4 | 4 | 2.9 |

Figure 16:
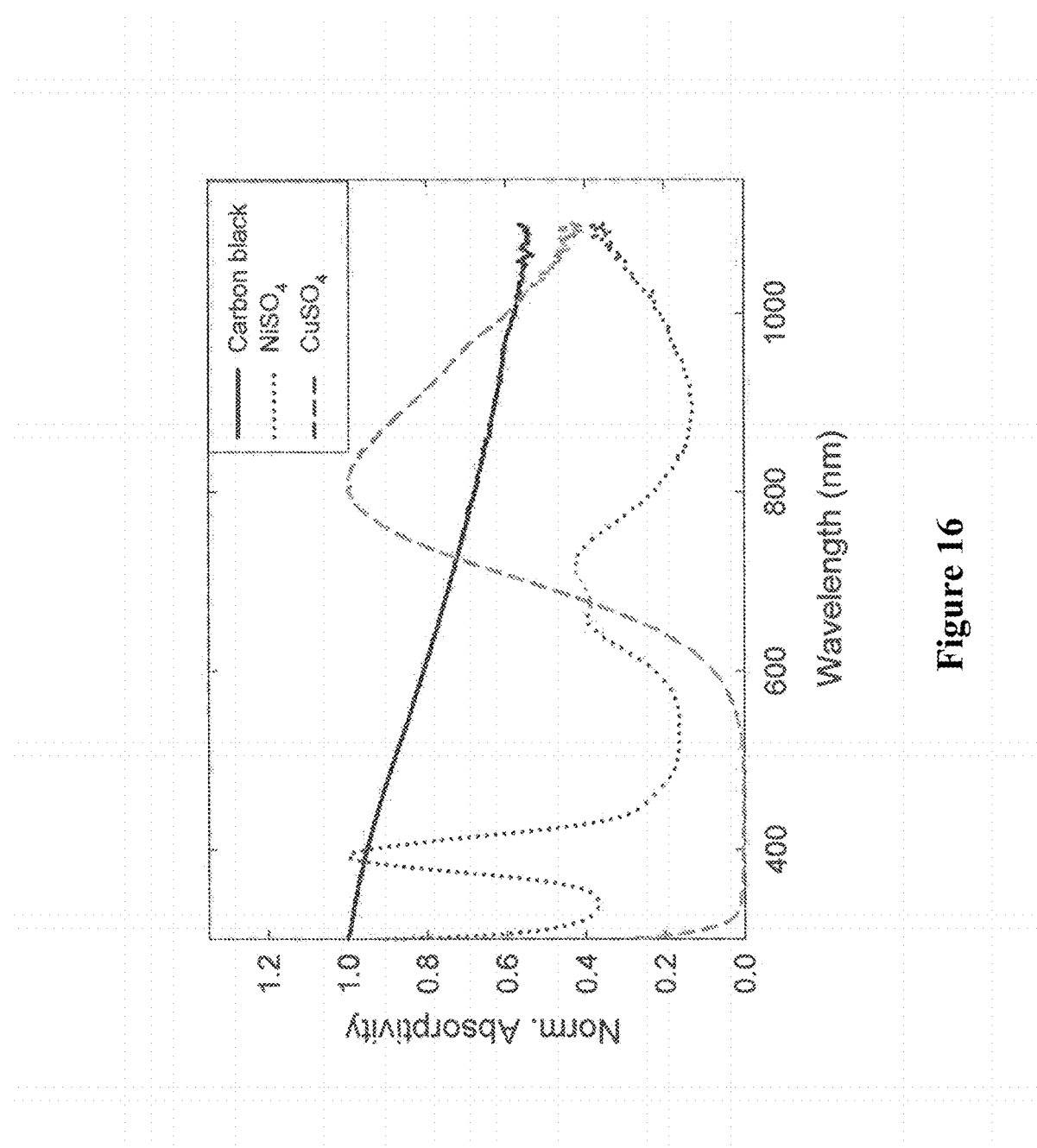
FIG. 16 illustrates an embodiment of the normalized absorption spectra of an embodiment of aqueous solutions of carbon black, NiSO4 and CuSO4.

In an embodiment, NiSO$_4$ and a mixture of CuSO$_4$ and aqueous suspensions of carbon black in 1% CTAB/water mixture are used to model arteries and veins. In an embodiment, a NiSO$_4$ solution, a CuSO$_4$ solution and an aqueous suspension of carbon black are prepared. In an embodiment, the carbon black solution is vigorously sonicated for 5-10 min to achieve a homogeneous suspension of carbon nanoparticles. The absorption spectra of the NiSO$_4$ solution, the CuSO$_4$ solution and the aqueous suspension of carbon black are measured. FIG. 16 illustrates an embodiment of the normalized absorption spectra of an embodiment of aqueous solutions of carbon black, NiSO4 and CuSO4. All solutions contain 1% CTAB. In an embodiment, the carbon black, NiSO4 and CuSO4 solutions are mixed in the proportions necessary to obtain absorptivity coefficient $\mu_a$ values listed in Table 4 at two wavelengths, 757 nm and 1064 nm, after gel preparation to create a vein model solution and an artery model solution. In an embodiment, volumetric expansion after addition of gelatin (see below) is taken into account for accuracy. See FIG. 1B.

In an embodiment, gels of desired density are then prepared using a vein model solution and an artery model solution as a base. For example, to make 10% gelatin gels use:

50 ml of the vein model solution or the artery model solution;
5.56 g of gelatin;
100 mg of methyl parabene;
0.375 ml of 20% chlorhexidine digluconate solution in water; and
100 mg of CTAB.

Figure 17:
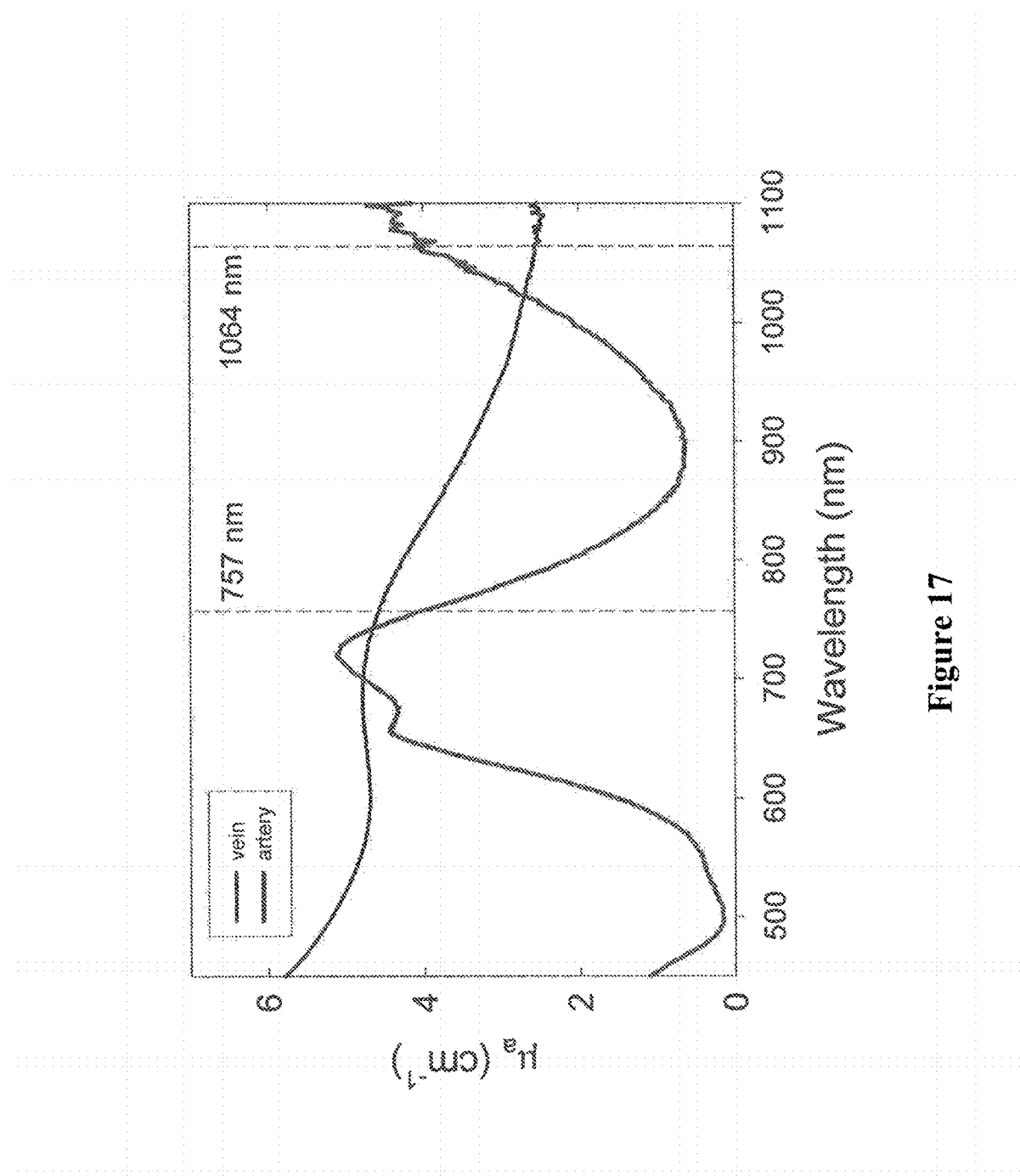
FIG. 17 illustrates an embodiment of the absorption spectra exhibited by vein and artery gels prepared according to the methods of the present disclosure.

The vein model solution or the artery model solution is heated to 30-35° C., and CTAB and preservatives are added and fully dissolved while mixing. Gelatin is then added while mixing and the resulting mixture is heated to 40-50° C. with continuous mixing to fully dissolve the gelatin. In an embodiment, the mass of the absorptivity coefficient $\mu_a$ is monitored and water is added as necessary to avoid errors due to water evaporation. In an embodiment, To air bubbles are removed from the gelatin mixture by placing samples in a sonicator bath to lift all the bubbles to the top where such bubbles can be manually remove them from the mixture. Absorption spectra of the gelatin mixture can be measured, and the absorptivity coefficient $\mu_a$ values of the gelatin mixture can be further corrected by adding necessary amounts of water and gelatin to the mixture. FIG. 17 illustrates an embodiment of the absorption spectra exhibited by vein and artery gelatin mixtures prepared according to the methods described above.

Note that the absorption spectra of the components may shift due to the interaction with the gelatin matrix or preservatives. In the illustrated embodiment described above, a noticeable blue-shift in the absorption spectra of CuSO$_4$ is observed after addition of chlorhexidine digluconate. The maximum of the observed CuSO$_4$ absorption spectrum shifts towards 760 nm, which is a wavelength of interest. In an embodiment, to prevent the dyes in the vein and artery models from spreading throughout a whole phantom, the liquid gelatin mixtures can be placed inside polyethylene capillaries. The use of capillaries may not be necessary if only nanoparticles are used for absorptivity coefficient $\mu_a$ adjustments since nanoparticles' diffusion is stopped in a gelatin matrix of a phantom.

Referring back to FIG. 14, in operation 1420 of the method, benign and malignant tumor models are prepared. Note that optical properties of benign and malignant tumors may vary substantially, thus only one example with selected absorptivity coefficients is described below, although it should be understood that, utilizing the compositions and methods described herein, tumor models exhibiting a wide variety of absorptivity coefficients can be created, as will be readily apparent to those skilled in the art.

In one example, it is well known that, due to angiogenesis, tumors typically have increased blood content relative to surrounding tissues. It is also known that malignant tumors typically exist in a locally hypoxic environment, and therefore the absorptivity spectra of such tumors will be similar to that of a vein. For benign tumor models, the similarity with absorption spectra of an artery is assumed. Table 5, below, summarizes the desired $\mu'_s$ and $\mu_a$ parameters in at least some embodiments of benign and malignant tumor models.

TABLE 5

Target $\mu_a$ and $\mu_s'$ Values in Tumor Models at Selected Wavelengths.

| Wavelength | Benign $\mu_a$, cm$^{-1}$ | Malignant $\mu_a$, cm$^{-1}$ | $\mu_s'$, cm$^{-1}$ |
| --- | --- | --- | --- |
| 757 nm | 0.25 | 0.5 | 9 |
| 1064 nm | 0.25 | 0.25 | 6 |

In an embodiment, the vein and/or artery model solutions described with respect to operation 1410 above can be used to create various tumor model solutions. In an embodiment, tumor model solutions are diluted with aqueous solution of 1% CTAB to match the desired absorptivity coefficient $\mu_a$ values, taking into account volumetric expansion after addition of gelatin. Thus, for example for making a 10% gel (expansion coefficient 1.088), tumor model solutions with absorptivity coefficient $\mu_a$ values of 0.27 and 0.54 cm−1 at 757 nm are prepared. In an embodiment, to prepare a specific type of gelatin matrix, 46 mg of TiO$_2$ is suspended in 10 ml of a tumor model solution by vigorously sonication the mixture for 5-10 min, creating a TiO$_2$ suspension. One ml of the tumor model solution is then used to suspend 100 mg of polyethylene microspheres with diameters 10-150 (Cospheric), creating a microsphere suspension. In an embodiment, 70 mg, 15 mg and 15 mg of samples of microspheres with dimensions of 10-106, 106-125 μm, and 125-150 μm, respectively are used to create the suspension.

Figure 18:
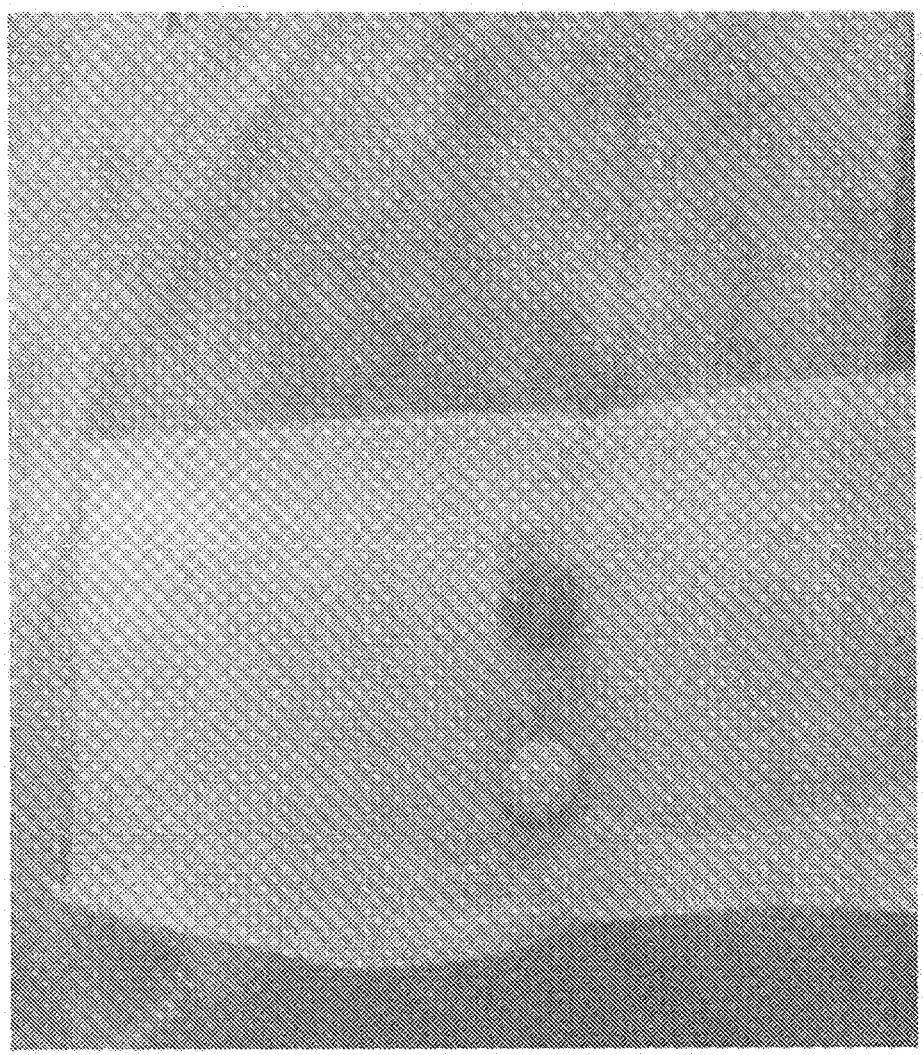
FIG. 18 illustrates embodiments of tumor models with $\mu_a$ as shown in Table 1, TiO2 concentration of 0.85 mg/ml and concentration of polyethylene microspheres of 1.8 mg/ml.

One hundred mg of methyl parabene, 0.375 ml of 20% chlorhexidine digluconate solution are then added to 39 ml of the tumor model solution and are dissolved while mixing. The resulting mixture is heated to 40-50° C. and 5.56 g of gelatin is added while mixing, allowing the gelatin to dissolve completely, thereby creating a gelatin mixture. The microsphere suspension is added to the to the gelatin mixture while mixing. The TiO2 suspension is added to the gelatin mixture while mixing. In an embodiment, the resulting mixture is sealed inside a thin latex or polyethylene membrane and allowed to cool until it gels. FIG. 18 illustrates embodiments of tumor models with absorptivity coefficient $\mu_a$ as shown in Table 1, TiO2 concentration of 0.85 mg/ml and concentration of polyethylene microspheres of 1.8 mg/ml.

In operation 1430 of the method, a bulk gelatin matrix is then prepared. The exemplary phantom whose creation is described below is a human breast phantom. In an embodiment, using published data on the composition of the breast, it is estimated that average absorptivity coefficient $\mu_a$ values may appear in the range 0.06-0.09 and 0.08-0.12 cm−1 at 757 and 1064 nm, respectively (FIG. 5b). For 15% gelatin, the absorptivity coefficient $\mu_a$ at 757 and 1064 nm are 0.05±0.01 and 0.12±0.01 cm−1. Thus, the absorptivity background in the gelatin matrix is very close to real breast tissue and does not need to be adjusted.

In an embodiment, a bulk gelatin matrix is be created using 900 ml of water, 159 g of gelatin, 0.87 g of TiO2, 2.1 g of CTAB, 2.1 g of methyl parabene, 7.76 ml of 20% chlorhexidine solution and 1.8 g of polyethylene microspheres with diameter 10-150 μm. A base solution is created by dissolving CTAB, methyl parabene, and chlorhexidine digluconate in water. 100 ml and 50 ml of the base solution are set aside for suspending TiO2 and polyethylene microspheres. Gelatin is added to the remaining base solution while mixing, allowing gelatin to fully dissolve, thereby creating a bulk gelatin solution. To remove air bubbles in the bulk gelatin solution, the container in which the bulk gelatin solution is prepared into a bath sonicator and sonicated for several minutes. Bubbles rise to the top and are removed manually. Alternatively, the bulk gelatin solution can be held under low pressure conditions until bubbles disappear.

Microspheres are then added to 50 ml of the base solution and sonicated to disperse microspheres, creating a microsphere suspension. The microsphere suspension is then mixed into the bulk gelatin solution. The bulk gelatin solution is then allowed to cool to ~30-40 C while mixing. The TiO$_2$ is then suspended in 100 ml of the base solution using 5-10 minutes of ultrasonic treatment in a bath sonicator, creation a TiO$_2$ suspension. The TiO$_2$ suspensio is then mixed into the bulk gelatin solution. At this point, the bulk gelatin solution is ready to be poured into a phantom mold.

In operation 1440 of the process, a phantom is assembled using the artery and vein models, the benign and malignant tumor models and the bulk gelatin matrix. In an embodiment, blood vessel and tumor models can be affixed inside the mold with strings or other similar means. The mold is filled with the bulk gelatin solution prepared in operation 1430 and allowed to gel. The phantom is then sealed to prevent liquid evaporation.

Figure 19A:
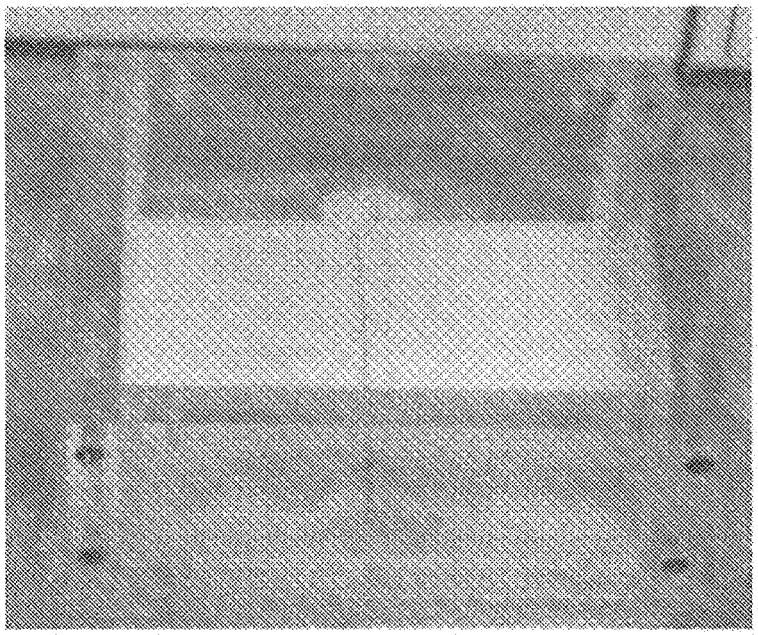
FIG. 19A illustrates the first operation of an assembly of a phantom in layers where artery and vein models are immobilized in the mold and a first layer is poured and allowed to gel.

Alternatively, the phantom may be assembled in layers as shown in FIG. 19A-D. FIG. 19A illustrates the first operation of an assembly of a phantom in layers where artery and vein models are immobilized in the mold and the first layer is poured and allowed to gel. In an embodiment, the first layer of the gelatin is poured into the mold up to the level where tumor models need to be placed and allow to gel.

Figure 19B:
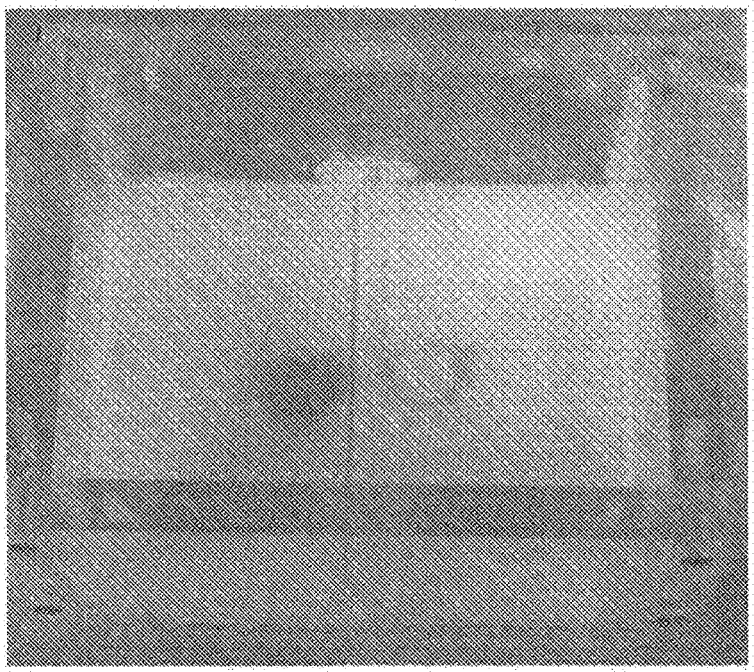
FIG. 19B illustrates the second operation of an assembly of a phantom in layers where tumor models are placed into the mold and partially covered with a second layer of gelatin.

FIG. 19B illustrates the second operation of an assembly of a phantom in layers where tumor models are placed into the mold and partially covered with a second layer of gelatin. Note, that due to difference in density, the tumor models may float. To avoid this, it is advisable not to cover the tumor models completely, but only to ~90% of the tumor models' height. The second layer is allowed to gel. If the targets are small, third intermediate layer may be poured to avoid melting the layer of gelatin that holds targets.

Figure 19C:
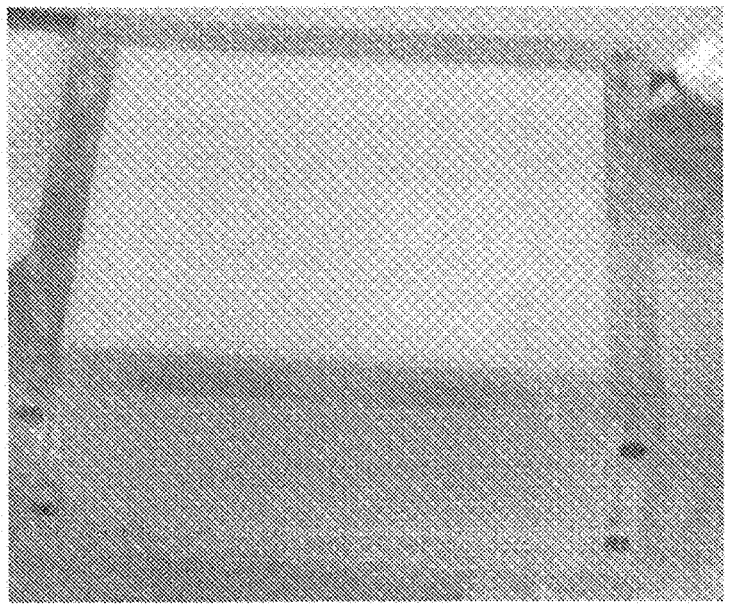
FIG. 19C illustrates the third operation of an assembly of a phantom in layers where mold is filled with gelatin solution and allowed to gel.
Figure 19D:
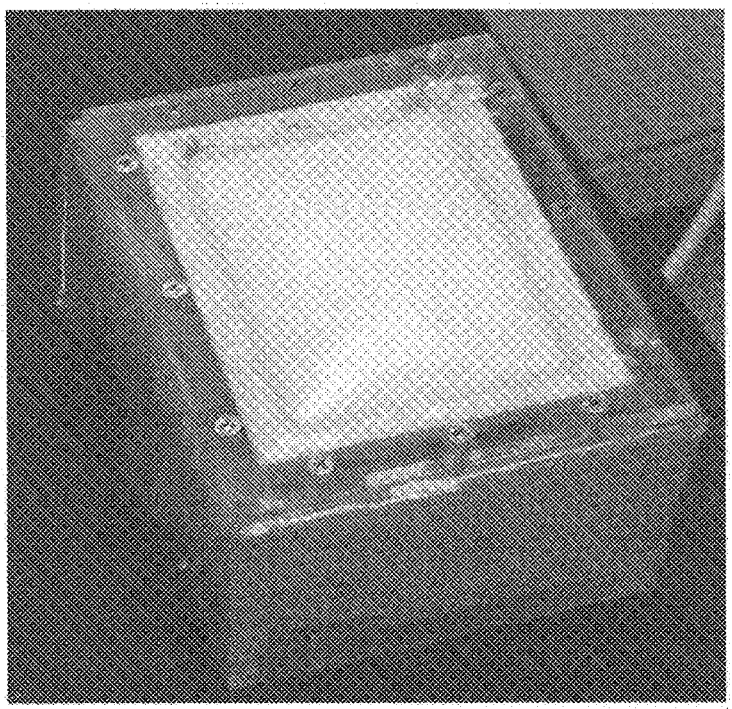
FIG. 19D illustrates an embodiment of a fully assembled phantom assembled according to the operations shown in FIGS. 19A-C.

FIG. 19C illustrates the third operation of an assembly of a phantom in layers where mold is filled with gelatin solution and allowed to gel. In an embodiment, the mold is filled completely and sealed, and the phantom is cooled to ~4° C. for 2-12 hours. FIG. 19D illustrates an embodiment of a fully assembled phantom assembled according to the operations shown in FIGS. 19A-C above.

An Illustrative Demonstration of a Phantom Developed Using an Embodiment of the Compositions and Methods Disclosed Above An exemplary dual modality opto-acoustic phantom was developed with optical and acoustic properties matching breast tissues with blood vessels (artery and vein) and tumors (malignant and benign) utilizing the compositions and methods described above. Optical properties in the desirable wavelength range and acoustic properties in the desirable range of ultrasonic frequencies in the resulting phantom match or closely simulate that of human breast tissue.

Figure 20:
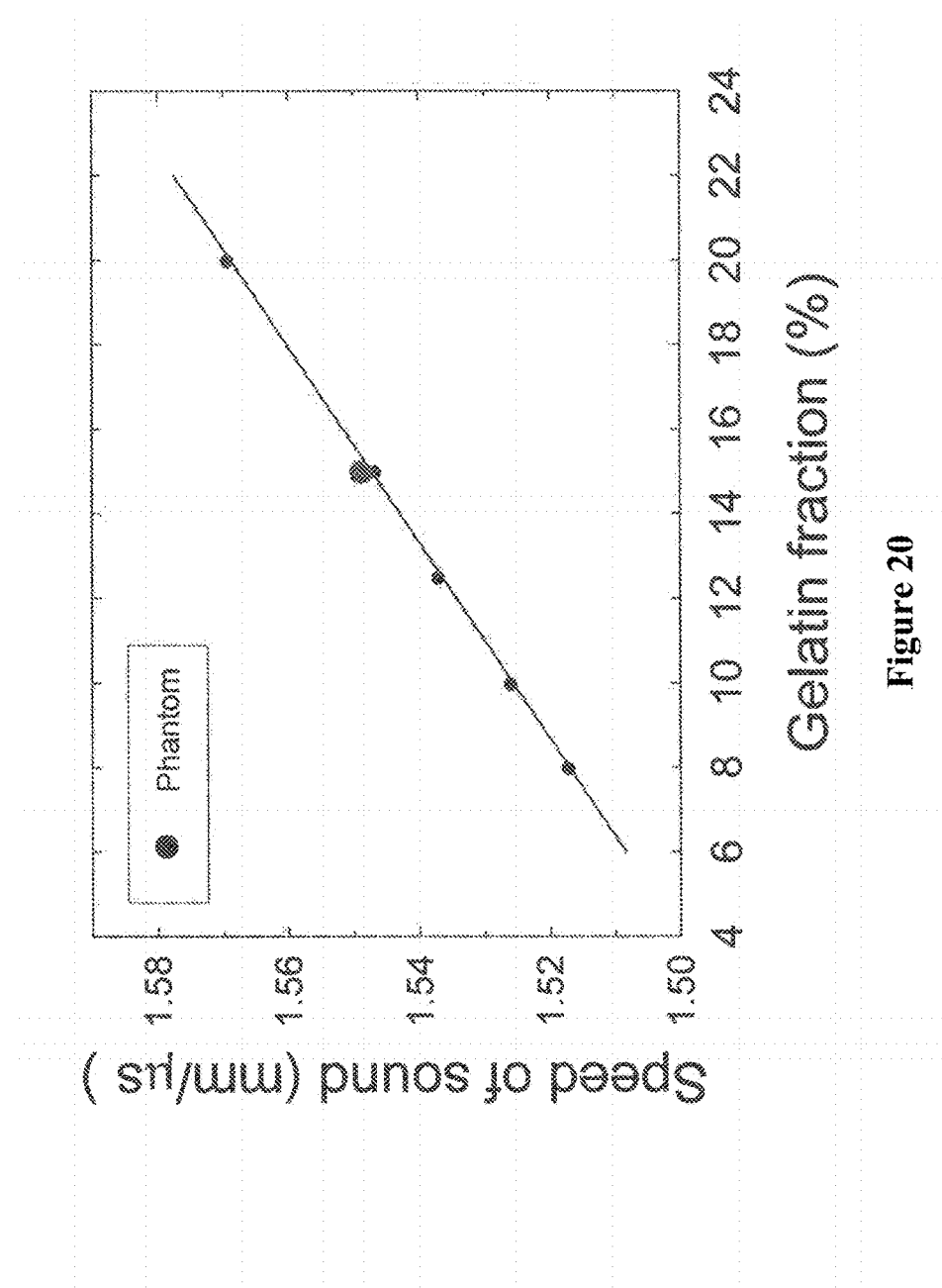
FIG. 20 illustrates the measured speed of sound in the bulk matrix of an exemplary dual modality opto-acoustic phantom.
Figure 21:
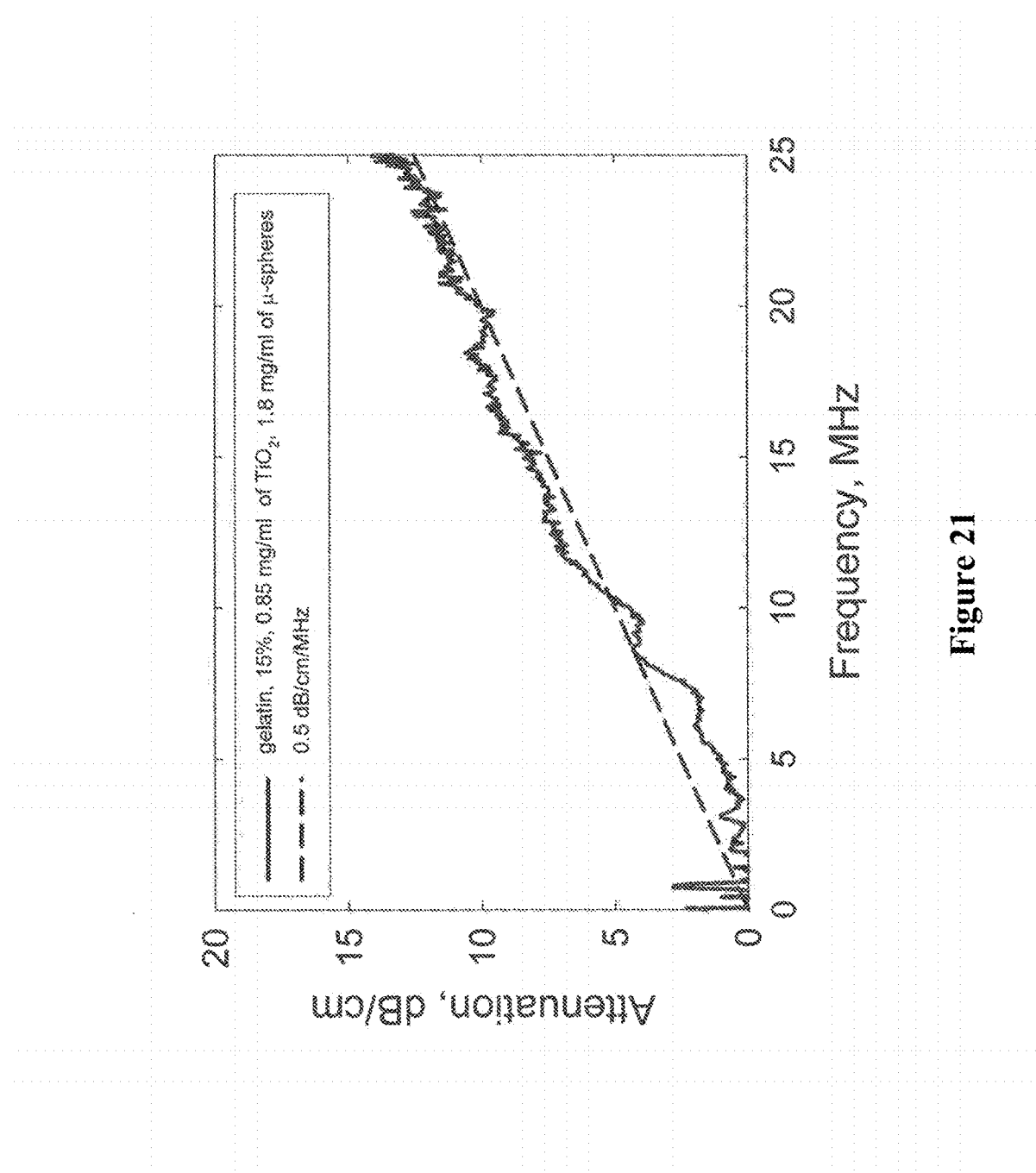
FIG. 21 illustrates the measured acoustic attenuation of the bulk gelatin matrix of an exemplary dual modality opto-acoustic phantom.
Figure 22A:
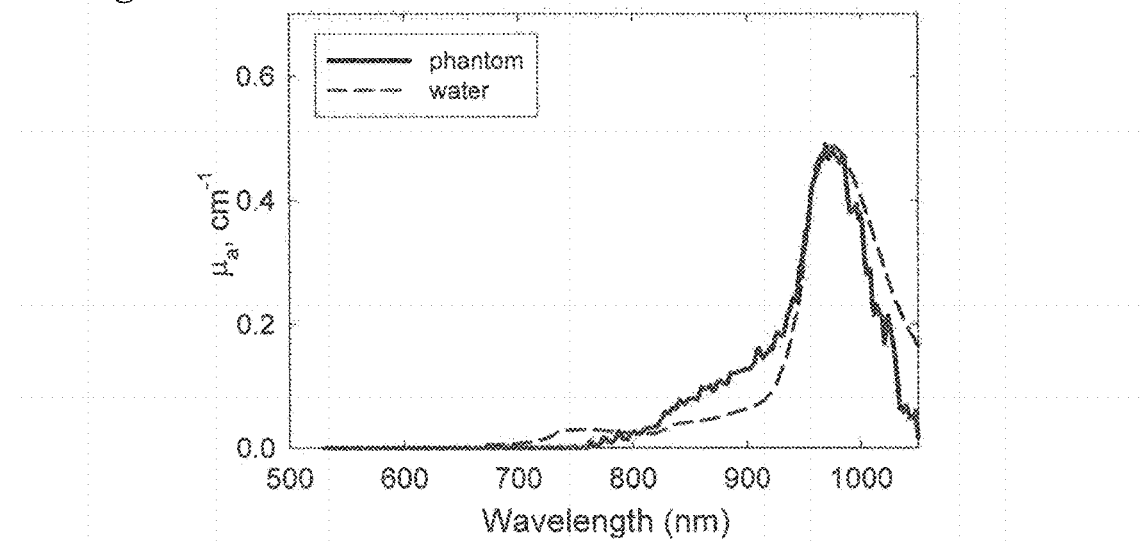
FIG. 22A illustrates the absorption background $\mu_a$ of the bulk gelatin matrix of the exemplary dual modality opto-acoustic phantom.
Figure 22B:
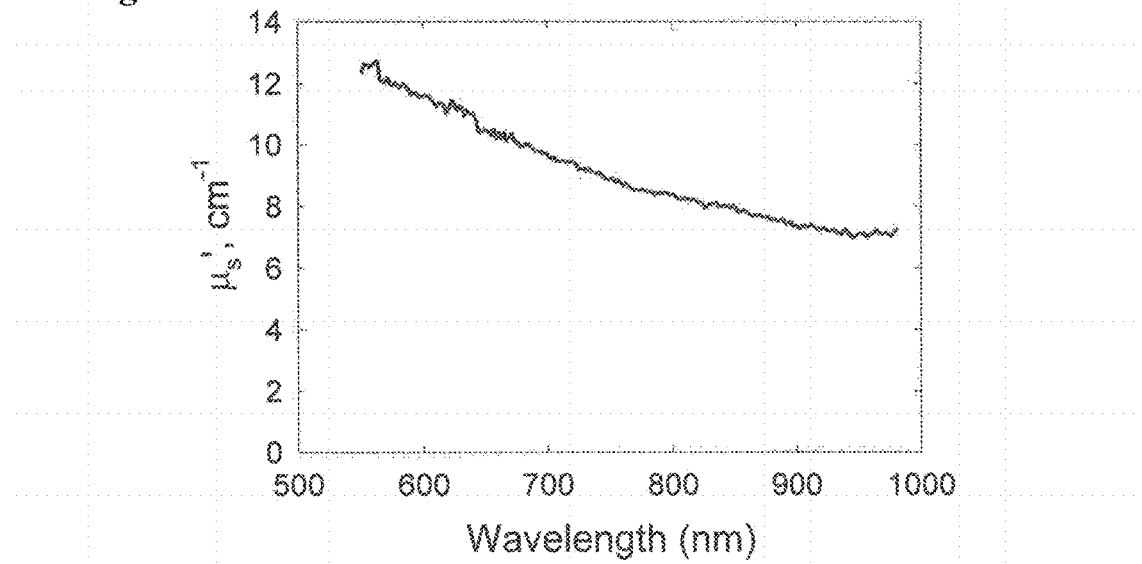
FIG. 22B illustrates the reduced scattering coefficient $\mu'_s$ (8.7 cm$^{-1}$ at 760 nm) of the bulk gelatin matrix of an exemplary dual modality opto-acoustic phantom.
Figure 22C:
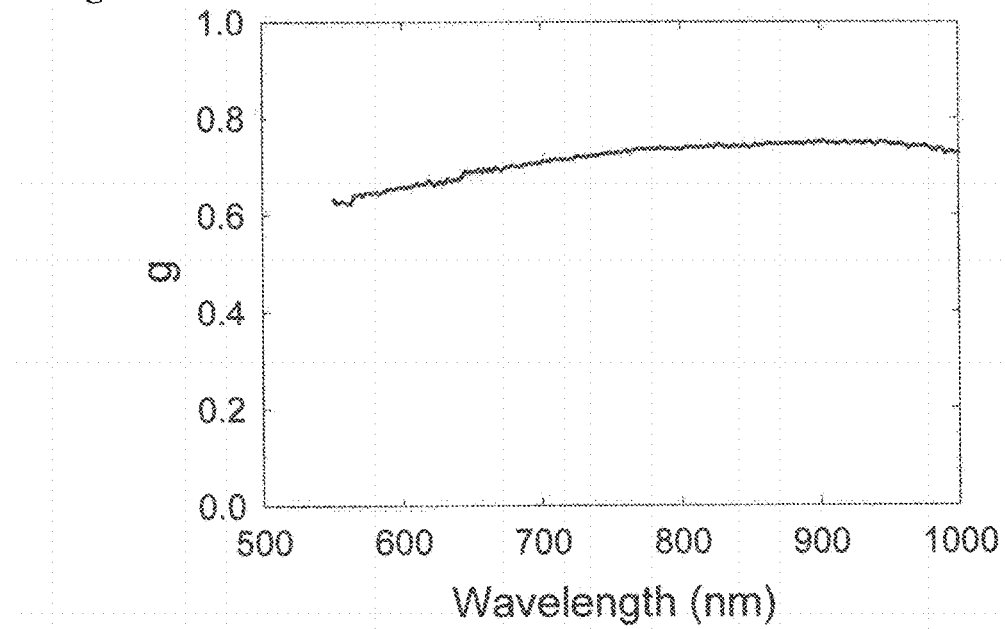
FIG. 22C illustrates the optical anisotropy factor g of the bulk gelatin matrix of an exemplary dual modality opto-acoustic phantom.

FIGS. 20, 21 and 22A-C illustrate acoustic and optical properties of the exemplary dual modality opto-acoustic phantom. FIG. 20 illustrates the measured speed of sound in the bulk matrix of the exemplary dual modality opto-acoustic phantom. FIG. 21 illustrates the measured acoustic attenuation of the bulk gelatin matrix of the exemplary dual modality opto-acoustic phantom. FIG. 22A illustrates the absorptivity coefficient $\mu_a$ of the bulk gelatin matrix of the exemplary dual modality opto-acoustic phantom. Note that the absorptivity coefficient $\mu_a$ of the bulk gelatin matrix is very similar to that of a pure water. FIG. 22B illustrates the reduced scattering coefficient $\mu'_s$ (8.7 cm$^{-1}$ at 760 nm) of the bulk gelatin matrix of the exemplary dual modality opto-acoustic phantom. FIG. 22C illustrates the optical anisotropy factor g of the bulk gelatin matrix of the exemplary dual modality opto-acoustic phantom.

Figure 23B:
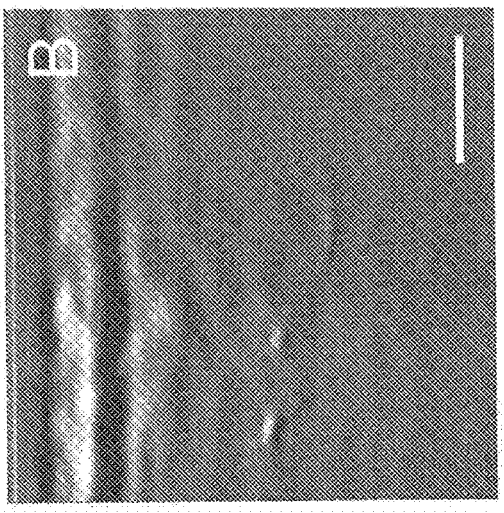
FIG. 23B shows an optoacoustic image of an exemplary dual modality opto-acoustic phantom showing blood vessels and the tumor models inside the phantom.
Figure 23C:
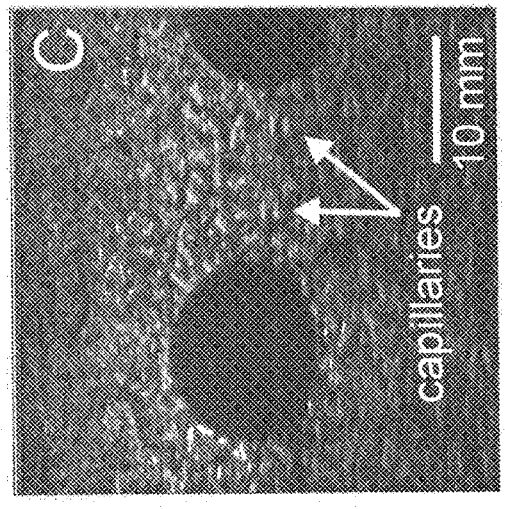
FIG. 23C shows an ultrasound image of an exemplary dual modality opto-acoustic phantom showing blood vessels and the tumor models inside the phantom.
Figure 23A:
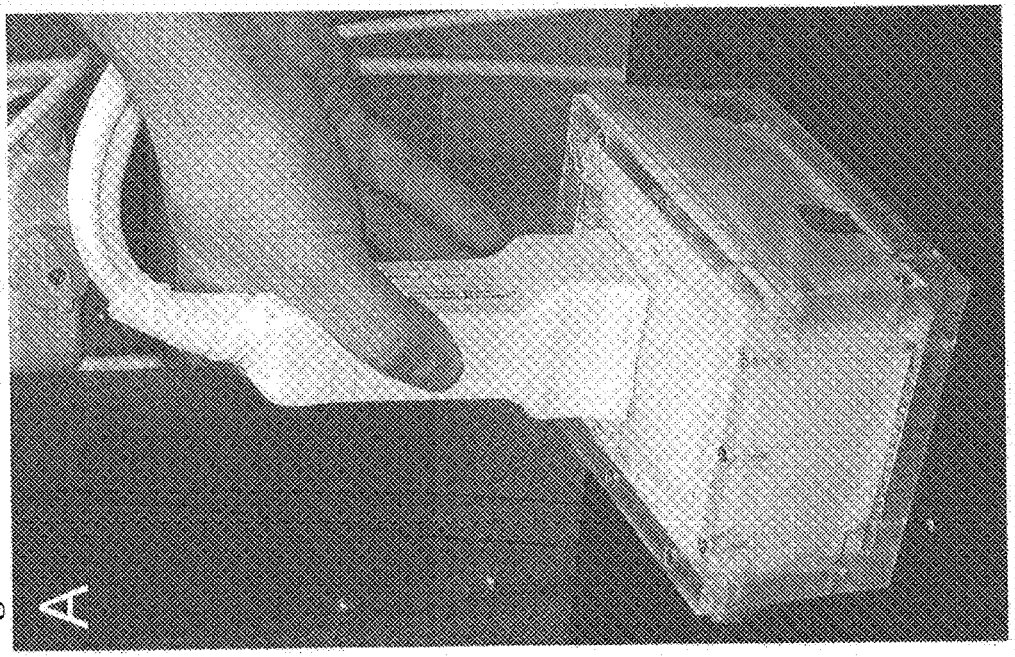
FIG. 23A shows an application of an opto-acoustic probe to the surface of an exemplary dual modality opto-acoustic phantom for the purpose of opto-acoustic imaging of the phantom.

FIGS. 23A-C illustrate results of opto-acoustic imaging of dual exemplary dual modality opto-acoustic phantom. FIG. 23A shows an application of an opto-acoustic probe to the surface of the exemplary dual modality opto-acoustic phantom for the purpose of opto-acoustic imaging of the phantom. FIG. 23B shows an optoacoustic image of the exemplary dual modality opto-acoustic phantom showing blood vessels and the tumor models inside the phantom. FIG. 23C shows an ultrasound image of the exemplary dual modality opto-acoustic phantom showing blood vessels and the tumor models inside the phantom.

Figure 24B:
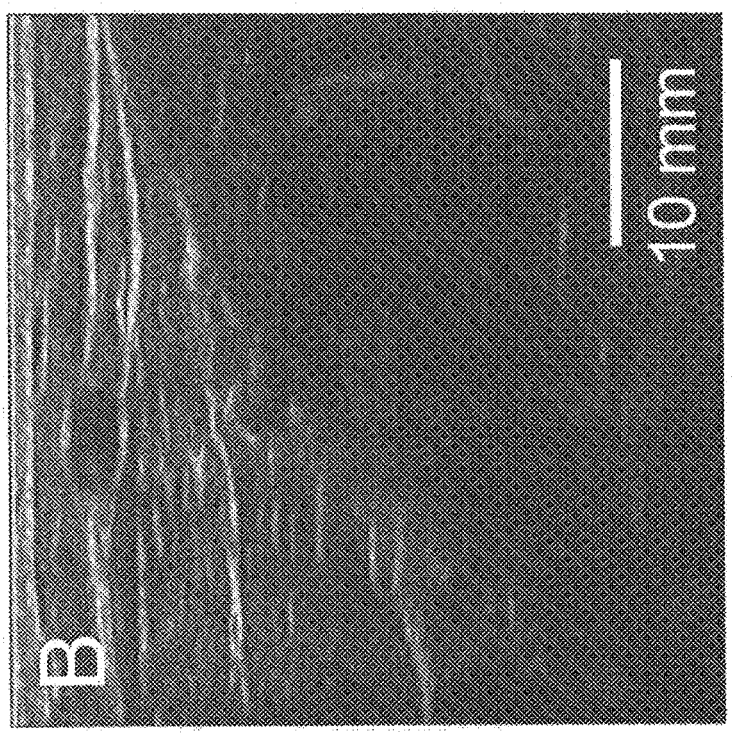
FIG. 24B shows an ultrasound image of exemplary living tissue in an arm.
Figure 24A:
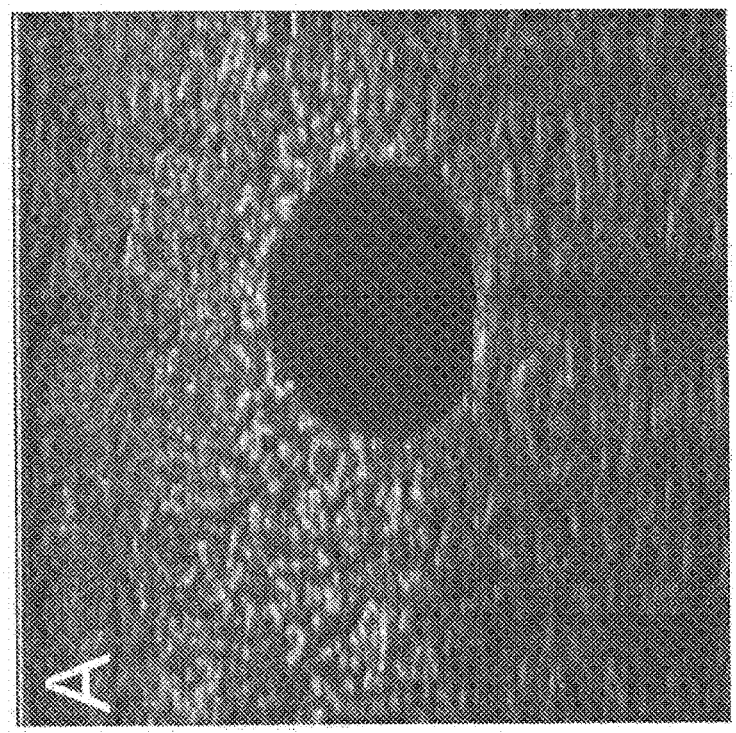
FIG. 24A shows an ultrasound image of an exemplary dual modality opto-acoustic phantom.

FIGS. 24A-B compare an ultrasound image of the exemplary dual modality opto-acoustic phantom (FIG. 24A) with that of living tissue in an arm (FIG. 24B). The background noise in the phantom appears not excessively higher as compare to ultrasound imaging of the arm.

CONCLUSION

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

We claim:

1. A phantom for medical imaging, comprising:
at least one background matrix comprising a first hydrogel with a first predefined proportion of gelatin to water and at least one first additive, such that the properties of the background matrix substantially match at least one optical property of a tissue and at least one acoustic property of the tissue;
at least one inclusion object embedded in the background matrix, the at least one inclusion object comprising a second hydrogel with a second predefined proportion of gelatin to water and at least one second additive, such that the properties of at least one inclusion object substantially matches at least one optical property of a tissue inclusion and at least one acoustic property of the tissue inclusion
wherein the at least one background matrix comprises a plurality of background matrices disposed in a plurality of layers that simulate a layered tissue, the plurality of background matrices each being formulated to match optical and acoustic properties of components of skin, the components of skin comprising epidermis, dermis, fat and muscle.

2. The phantom of claim 1, wherein
the at least one optical property of the tissue and the at least one optical property of the tissue inclusion relate to the spectral range of approximately 650 nm to 1250 nm, and wherein
the at least one acoustic property of the tissue and the at least one acoustic property of the tissue inclusion relate to the ultrasonic frequency range of 100 kHz to 20 MHz.

3. The phantom of claim 2, wherein
the at least one optical property of the tissue and the at least one optical property of the tissue inclusion is selected from the list: absorption coefficient, scattering coefficient and anisotropy factor, and wherein
the at least one acoustic property of the tissue and the at least one acoustic property of the tissue inclusion is selected from the list: speed of sound, density, acoustic attenuation and acoustic backscattering.

4. The phantom of claim 2, wherein
the at least one optical property of the tissue and the at least one optical property of the tissue inclusion comprises absorption coefficient, scattering coefficient and anisotropy factor, and wherein
the at least one acoustic property of the tissue and the at least one acoustic property of the tissue inclusion comprises speed of sound, density, acoustic attenuation and acoustic backscattering.

5. The phantom of claim 1, wherein the at least one first additive comprises at least one substance selected from the group consisting of TiO$_2$, surfactants, antibacterials, antifungals, polyethylene microspheres, and mixtures thereof.

6. The phantom of claim 1, wherein the at least one second additive is selected from the group consisting of NiSO$_4$, CuSO$_4$, carbon black, and mixtures thereof.

7. The phantom of claim 6, wherein the at least one first additive comprises at least one substance selected from the group consisting of TiO$_2$, surfactants, antibacterials, antifungals, polyethylene microspheres, and mixtures thereof.

8. The phantom of claim 1, wherein the inclusion object is an artery model, a vein model, a benign tumor model, or a malignant tumor model.

9. The phantom of claim 8, wherein
the inclusion object is an artery model or a vein model,
(i) the properties of the artery model comprising
a first absorption coefficient of approximately 4 $cm^{-1}$ at a first light wavelength of approximately 757 nm and
a second absorption coefficient of approximately 4 $cm^{-1}$ at a second light wavelength of approximately 1064 nm; and
(ii) the properties of the vein model comprising
a first absorption coefficient of approximately 4.7 $cm^{-1}$ at a first light wavelength of approximately 757 nm and
a second absorption coefficient of approximately 2.9 $cm^{-1}$ at a second light wavelength of approximately 1064 nm.

10. The phantom of claim 8, wherein
the inclusion object is a benign tumor model or a malignant tumor model,
(i) the properties of the benign tumor model comprising
a first absorption coefficient of approximately 0.25 $cm^{-1}$ at a first light wavelength of approximately 757 nm and a first scattering coefficient of approximately 9 $cm^{-1}$ at the first light wavelength;
a second absorption coefficient of approximately 0.25 $cm^{-1}$ at a second light wavelength of approximately 1064 nm and a second scattering coefficient of approximately 6 $cm^{-1}$ at the first light wavelength; and
(ii) the properties of the malignant tumor model comprising
a first absorption coefficient of approximately 0.50 $cm^{-1}$ at a first light wavelength of approximately 757 nm and a first scattering coefficient of approximately 9 $cm^{-1}$ at the first light wavelength;
a second absorption coefficient of approximately 2.5 $cm^{-1}$ at a second light wavelength of approximately 1064 nm and a second scattering coefficient of approximately 6 $cm^{-1}$ at the first light wavelength.

11. The phantom of claim 1, wherein
at least two of the plurality of background matrices comprise respective hydrogels having different proportions of gelatin and water.

12. The phantom of claim 1, wherein
the at least one background matrices is formulated to simulate a tissue having microheterogeneities, wherein the microheterogeneities are simulated by polyethylene microspheres of a plurality of densities.

13. The phantom of claim 1, wherein
the phantom is incased within a protective material at least one surface that is optically and acoustically transparent.

14. The phantom of claim 1, wherein the at least one inclusion is incased within a polymer membrane.

15. A phantom for medical imaging, comprising:
at least one background matrix comprising a first hydrogel with a first predefined proportion of gelatin to water and at least one first additive, such that the properties of the background matrix substantially match at least one optical property of a tissue and at least one acoustic property of the tissue; and
at least one inclusion object embedded in the background matrix, the at least one inclusion object comprising a second hydrogel with a second predefined proportion of gelatin to water and at least one second additive, such that the properties of at least one inclusion object substantially matches at least one optical property of a tissue inclusion and at least one acoustic property of the tissue inclusion;
wherein the inclusion object is an artery model or a vein model,
(i) the properties of the artery model comprising
a first absorption coefficient of approximately 4 $cm^{-1}$ at a first light wavelength of approximately 757 nm and
a second absorption coefficient of approximately 4 $cm^{-1}$ at a second light wavelength of approximately 1064 nm; and
(ii) the properties of the vein model comprising
a first absorption coefficient of approximately 4.7 $cm^{-1}$ at a first light wavelength of approximately 757 nm and
a second absorption coefficient of approximately 2.9 $cm^{-1}$ at a second light wavelength of approximately 1064 nm.

16. The phantom of claim 15, wherein the at least one background matrix comprises a plurality of background matrices disposed in a plurality of layers that simulate a layered tissue, the plurality of background matrices each being formulated to match optical and acoustic properties of components of skin, the components of skin comprising epidermis, dermis, fat and muscle.

17. The phantom of claim 15, wherein the at least one first additive comprises at least one substance selected from the group consisting of $TiO_2$, surfactants, antibacterials, antifungals, polyethylene microspheres, and mixtures thereof, and wherein the at least one second additive is selected from the group consisting of $NiSO_4$, $CuSO_4$, carbon black and mixtures thereof.

18. The phantom of claim 15, wherein the at least one background matrices is formulated to simulate a tissue having microheterogeneities, wherein the microheterogeneities are simulated by polyethylene microspheres of a plurality of densities.

19. A phantom for medical imaging, comprising:
at least one background matrix comprising a first hydrogel with a first predefined proportion of gelatin to water and at least one first additive, such that the properties of the background matrix substantially match at least one optical property of a tissue and at least one acoustic property of the tissue; and
at least one inclusion object embedded in the background matrix, the at least one inclusion object comprising a second hydrogel with a second predefined proportion of gelatin to water and at least one second additive, such that the properties of at least one inclusion object substantially matches at least one optical property of a tissue inclusion and at least one acoustic property of the tissue inclusion;
wherein the background matrix comprises at least two background matrices disposed in layers that simulate a layered tissue, the matrices comprising respective hydrogels having different proportions of gelatin and water.

20. The phantom of claim 19, wherein the inclusion object is an artery model, a vein model, a benign tumor model, or a malignant tumor model.

21. The phantom of claim 19, wherein
the at least one optical property of the tissue and the at least one optical property of the tissue inclusion is selected from the list: absorption coefficient, scattering coefficient and anisotropy factor, and wherein the at least one acoustic property of the tissue and the at least one acoustic property of the tissue inclusion is selected from the list: speed of sound, density, acoustic attenuation and acoustic backscattering.

22. The phantom of claim 19, wherein the at least one first additive comprises at least one substance selected from the group consisting of $TiO_2$, surfactants, antibacterials, antifungals, polyethylene microspheres, and mixtures thereof, and wherein the at least one second additive is selected from the group consisting of $NiSO_4$, $CuSO_4$, carbon black and mixtures thereof.

23. The phantom of claim 19, wherein
the plurality of background matrices are each formulated to match optical and acoustic properties of components of skin, the components of skin comprising epidermis, dermis, fat and muscle.

24. The phantom of claim 19, wherein
the at least one background matrices is formulated to simulate a tissue having microheterogeneities wherein the microheterogeneities are simulated by polyethylene microspheres of a plurality of densities.

25. A phantom for medical imaging, comprising:
at least one background matrix comprising a first hydrogel with a first predefined proportion of gelatin to water and at least one first additive, such that the properties of the background matrix substantially match at least one optical property of a tissue and at least one acoustic property of the tissue; and
at least one inclusion object embedded in the background matrix, the at least one inclusion object comprising a second hydrogel with a second predefined proportion of gelatin to water and at least one second additive, such that the properties of at least one inclusion object substantially matches at least one optical property of a tissue inclusion and at least one acoustic property of the tissue inclusion;
wherein the first additive comprises $TiO_2$, polyethylene microspheres, a surfactant, and a preservative, wherein the preservative is an antibacterial or an antifungal.

26. The phantom of claim 25, wherein the inclusion object is an artery model, a vein model, a benign tumor model, or a malignant tumor model.

27. The phantom of claim 25, wherein
the at least one optical property of the tissue and the at least one optical property of the tissue inclusion is selected from the list: absorption coefficient, scattering coefficient and anisotropy factor, and wherein
the at least one acoustic property of the tissue and the at least one acoustic property of the tissue inclusion is selected from the list: speed of sound, density, acoustic attenuation and acoustic backscattering.

28. The phantom of claim 25, wherein the at least one second additive is selected from the group consisting of $NiSO_4$, $CuSO_4$, carbon black and mixtures thereof.

29. The phantom of claim 25, wherein
the at least one background matrix comprises a plurality of background matrices disposed in a plurality of layers that simulate a layered tissue.

30. The phantom of claim 29, wherein
at least two of the plurality of background matrices comprise respective hydrogels having different proportions of gelatin and water.

31. The phantom of claim 29, wherein
the plurality of background matrices are each formulated to match optical and acoustic properties of components of skin, the components of skin comprising epidermis, dermis, fat and muscle.

32. The phantom of claim 25, wherein
the at least one background matrices is formulated to simulate a tissue having microheterogeneities, wherein the microheterogeneities are simulated by polyethylene microspheres of a plurality of densities.

33. A phantom for medical imaging, comprising:
at least one background matrix comprising a first hydrogel with a first predefined proportion of gelatin to water and at least one first additive, such that the properties of the background matrix substantially match at least one optical property of a tissue and at least one acoustic property of the tissue;
at least one inclusion object incased within a polymer membrane and embedded in the background matrix, the at least one inclusion object comprising a second hydrogel with a second predefined proportion of gelatin to water and at least one second additive, such that the properties of at least one inclusion object substantially matches at least one optical property of a tissue inclusion and at least one acoustic property of the tissue inclusion.

34. The phantom of claim 33, wherein the inclusion object is an artery model, a vein model, a benign tumor model, or a malignant tumor model.

35. The phantom of claim 33, wherein
the at least one optical property of the tissue and the at least one optical property of the tissue inclusion is selected from the list: absorption coefficient, scattering coefficient and anisotropy factor, and wherein
the at least one acoustic property of the tissue and the at least one acoustic property of the tissue inclusion is selected from the list: speed of sound, density, acoustic attenuation and acoustic backscattering.

36. The phantom of claim 33, wherein the at least one first additive comprises at least one substance selected from the group consisting of $TiO_2$, surfactants, antibacterials, antifungals, polyethylene microspheres, and mixtures thereof, and the at least one second additive is selected from the group consisting of $NiSO_4$, $CuSO_4$, carbon black and mixtures thereof.

37. The phantom of claim 33, wherein
the at least one background matrix comprises a plurality of background matrices disposed in a plurality of layers that simulate a layered tissue.

38. The phantom of claim 37, wherein
at least two of the plurality of background matrices comprise respective hydrogels having different proportions of gelatin and water.

39. The phantom of claim 37, wherein
the plurality of background matrices are each formulated to match optical and acoustic properties of components of skin, the components of skin comprising epidermis, dermis, fat and muscle.

40. The phantom of claim 33, wherein
the at least one background matrices is formulated to simulate a tissue having microheterogeneities, wherein the microheterogeneities are simulated by polyethylene microspheres of a plurality of densities.

* * * * *

UNITED STATES PATENT AND TRADEMARK OFFICE
CERTIFICATE OF CORRECTION

Page 1 of 1

PATENT NO. : 9,655,594 B2
APPLICATION NO. : 14/109816
DATED : May 23, 2017
INVENTOR(S) : Oraevsky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 469 days.

Signed and Sealed this
Seventeenth Day of October, 2017

Joseph Matal
*Performing the Functions and Duties of the
Under Secretary of Commerce for Intellectual Property and
Director of the United States Patent and Trademark Office*